US010705065B2

(12) United States Patent
Shalom et al.

(10) Patent No.: US 10,705,065 B2
(45) Date of Patent: Jul. 7, 2020

(54) DEVICES FOR USE IN DETECTION AND IDENTIFICATION OF TRACE AND VAPOR AMOUNTS OF SUBSTANCES

(71) Applicant: M.S.TECH LTD., Herzliya (IL)

(72) Inventors: Moshe Shalom, Herzliya (IL); Lev Dayan, Holon (IL); Doron Shalom, Herzliya (IL); Michael Sister, Holon (IL); Veniamin Tsveer, Rehovot (IL); Vladimir Sergeyev, Rehovot (IL)

(73) Assignee: M.S.TECH LTD., Herzliya (IL)

( * ) Notice: Subject to any disclaimer, the term of this patent is extended or adjusted under 35 U.S.C. 154(b) by 226 days.

(21) Appl. No.: 14/912,271

(22) PCT Filed: Aug. 14, 2014

(86) PCT No.: PCT/IL2014/050737
§ 371 (c)(1),
(2) Date: Feb. 16, 2016

(87) PCT Pub. No.: WO2015/022694
PCT Pub. Date: Feb. 19, 2015

(65) Prior Publication Data

US 2016/0209382 A1 Jul. 21, 2016

(30) Foreign Application Priority Data

Aug. 15, 2013 (IL) .......................................... 227973

(51) Int. Cl.
*G01N 1/24* (2006.01)
*G01N 33/00* (2006.01)
(Continued)

(52) U.S. Cl.
CPC ........... *G01N 33/0031* (2013.01); *G01N 1/04* (2013.01); *G01N 1/2273* (2013.01); *G01N 1/24* (2013.01);
(Continued)

(58) Field of Classification Search
None
See application file for complete search history.

(56) References Cited

U.S. PATENT DOCUMENTS 4,154,794 A * 5/1979 Clyne .................. G01N 1/2258
222/209
4,818,348 A 4/1989 Stetter
(Continued)

FOREIGN PATENT DOCUMENTS

WO 2009/053957 A2 4/2009

OTHER PUBLICATIONS

International Search Report for PCT/IL2014/050737 dated Dec. 2, 2014.

(Continued)

*Primary Examiner* — Paul S Hyun
(74) *Attorney, Agent, or Firm* — Browdy and Neimark, PLLC

(57) ABSTRACT

Disclosed are substance detection and identification devices, and methods of using them for detection and identification of substances in ambient surroundings, on surfaces of objects, inside closed items or in fluids. A substance detection and identification device may comprise a housing, an opening in the housing for passage of sample material therethrough, a sensing unit located in the housing and an array of sensing elements configured and operable to interact with sample material in the vicinity thereof for detecting one or more specific substances and generating sensing data indicative thereof. A sample path defined in the housing between the opening and the sensing unit is used for facilitating flow of the sample material towards the sensing unit. A gas inlet assembly provided in the housing is configured for providing a predetermined supply of the sample material to the sensing elements in the sensors array, to thereby enable a predetermined time pattern of the
(Continued)

sensing data from the array of sensing elements. A heating unit may be provided in the housing for heating the sensing elements.

37 Claims, 17 Drawing Sheets

(51) Int. Cl.

*G01N 1/04* (2006.01)
*G01N 29/036* (2006.01)
*G01N 1/22* (2006.01)
*G01N 29/22* (2006.01)
*G01N 33/22* (2006.01)

(52) U.S. Cl.

CPC ......... *G01N 29/036* (2013.01); *G01N 29/222* (2013.01); *G01N 33/0009* (2013.01); *G01N 33/225* (2013.01); *G01N 33/0016* (2013.01); *G01N 33/0021* (2013.01); *G01N 33/22* (2013.01); *G01N 2033/0019* (2013.01)

(56) References Cited

U.S. PATENT DOCUMENTS

| | | | | |
|---|---|---|---|---|
| 5,139,889 | A | 8/1992 | Conrad | |
| 5,469,369 | A | 11/1995 | Rose-Pehrsson et al. | |
| 5,859,375 | A | 1/1999 | Danylewych-May et al. | |
| 6,085,576 | A | 7/2000 | Sunshine | |
| 6,455,319 | B1 * | 9/2002 | Lewis .................. | G01N 27/126 422/68.1 |
| 6,526,828 | B1 | 3/2003 | Dayan et al. | |
| 6,642,513 | B1 | 11/2003 | Jenkins et al. | |
| 6,883,364 | B2 | 4/2005 | Sunshine | |
| 7,089,780 | B2 | 8/2006 | Sunshine et al. | |
| 7,159,463 | B2 | 1/2007 | Dayagi et al. | |
| 7,795,008 | B2 | 9/2010 | Dayagi et al. | |
| 2001/0039824 | A1 | 11/2001 | Sunshine et al. | |
| 2001/0041366 | A1 | 11/2001 | Lewis et al. | |
| 2004/0110300 | A1 * | 6/2004 | Carpenter ................ | G01N 1/40 436/34 |
| 2007/0068223 | A1 * | 3/2007 | Chen .................... | G01N 1/2211 73/30.01 |
| 2011/0184397 | A2 * | 7/2011 | Dayan .................. | G01N 29/036 606/20 |

OTHER PUBLICATIONS

Partial Supplemental European for European Application No. 14836154 dated Jan. 30, 2017.

* cited by examiner

Fig. 8C
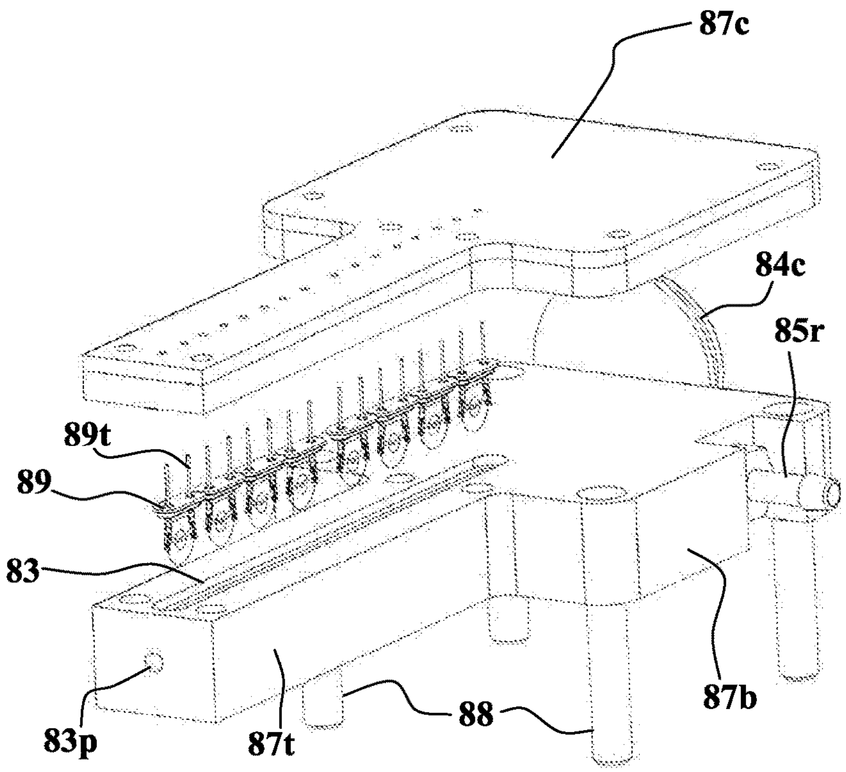
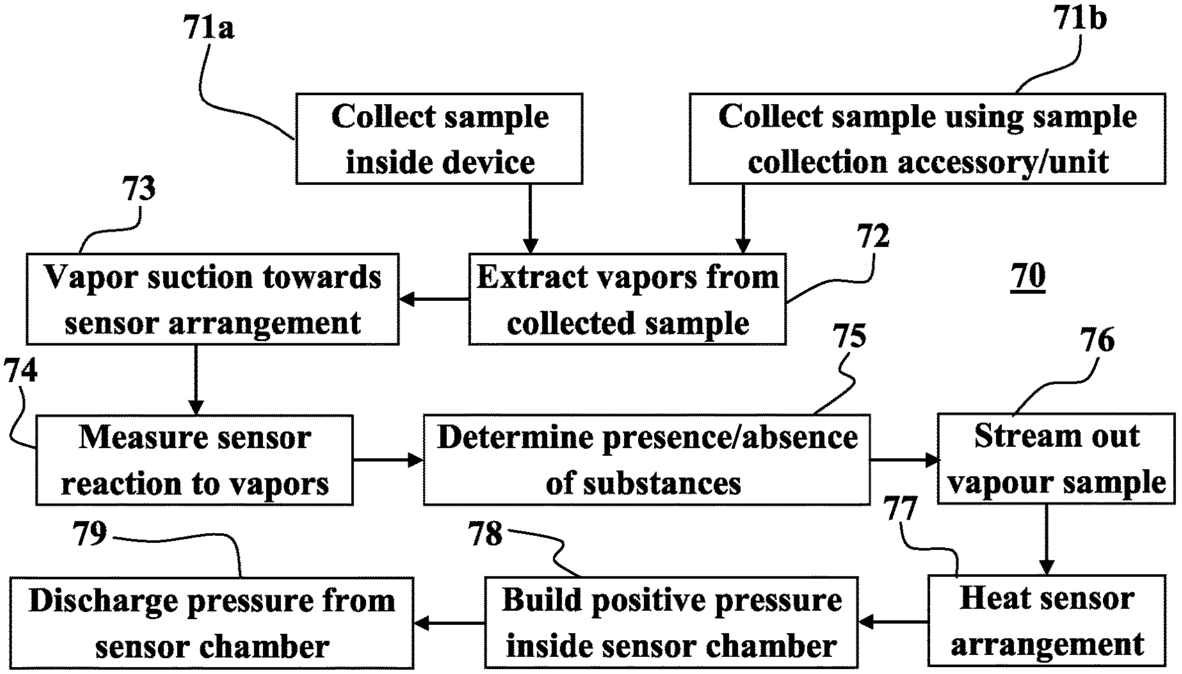
Fig. 9

DEVICES FOR USE IN DETECTION AND IDENTIFICATION OF TRACE AND VAPOR AMOUNTS OF SUBSTANCES

TECHNOLOGICAL FIELD

The invention is generally in the field of sensing techniques for detection and identification of substances in ambient surroundings, on surfaces of objects, inside closed items or in fluids.

BACKGROUND

Techniques for detection and identification of substances are exploited nowadays in a variety of implementations aiming at detection of trace amounts of particular materials, such as, but not limited to, narcotics, explosives, toxic industrial chemicals and minerals (e.g., surface geochemical exploration, such as oil and gas exploration).

Some exemplary implementations of such substance detection techniques are disclosed in the following patent publications.

U.S. Pat. No. 5,859,375 describes a handheld sampling apparatus having a handle, a head connected to the handle and a mechanism for retaining a substrate on the head in a form of a flexible sheet, which is mounted so as to present a collection portion thereof for collection of a sample. The substrate is configured to be readily fitted into an inlet portion of an analyzer. The apparatus enables an area to be sampled quickly and efficiently, while keeping a user's hands away from the surface, which enables otherwise inaccessible areas to be sampled.

U.S. Pat. No. 6,642,513 discloses sample traps or wipes for a detection system for detecting contraband materials. The sample trap is formed from an open weave glass fabric coated with a thin layer of Teflon and roughened to cut through the surface of Teflon and to break some of the glass fibers. Alternatively, the sample trap is non-woven felt fabric made of high temperature polyamide fiber. The sample traps are used in a detector, such as an ion trap mobility spectrometer. The detector includes a desorber, which feeds dry air from a manifold above and below the sample trap through a series of holes along the mouth of the desorber. The dry air passes through the trap and purges out unwanted atmospheric constituents that could otherwise affect the performance of the detector. The purged air passes to the outside atmosphere, thus creating a dry curtain at the entry to the desorber.

US Patent publication No. 2001/039824 describes a vapor sensing device that is sufficiently small and lightweight to be handheld, and also modular so as to allow the device to be conveniently adapted for use in sensing the presence and concentration of a wide variety of specified vapors. The device provides these benefits using a sensor module that incorporates a sample chamber and a plurality of sensors located on a chip releasably carried within or adjacent to the sample chamber. Optionally, the sensor module can be configured to be releasably plugged into a receptacle formed in the device. Vapors are directed to pass through the sample chamber, whereupon the sensors provide a distinct combination of electrical signals in response to each vapor. The sensors of the sensor module can take the form of chemically sensitive resistors having resistances that vary according to the identity and concentration of an adjacent vapor. These chemically sensitive resistors can each be connected in series with a reference resistor, between a reference voltage and ground, such that an analog signal is established for each chemically sensitive resistor. The resulting analog signals are supplied to an analog-to-digital converter, to produce corresponding digital signals. These digital signals are appropriately analyzed for vapor identification.

General Description

There is a need in the art for compact and portable substance detection equipment usable for determining the presence or absence of specific substances in ambient air, on surfaces of objects and/or skin tissue, inside closed articles, and in fluid matter. It would also be advantageous to compactly arrange such substance detection equipment to provide a handheld portable substance detection device capable of rapidly detecting and identifying the presence of certain materials in ambient air or on/in inspected items. Design and development of such compact substance detection devices for rapidly and reliably collecting a sample, analyzing, detecting and identifying the presence of specific substances contained therein, are difficult and complex. Particularly, such devices should compactly incorporate sample collection and extraction functionalities, provide a sensor arrangement that can guarantee interaction of sampled material with one or more substance sensing elements to reliably detect the presence of specific substances therein, and enable fast and efficient discharge of the inspected sample from the sensor arrangement, and proper cleaning/decontamination of the substance sensing elements to remove residuals of inspected materials to permit instantly carrying out a new substance detection cycle.

The inventors of the present invention have developed a novel portable handheld substance detection device configured and operable to rapidly collect sample material and/or vapors, produce vapors from the collected sample (if so needed) and introduce the produced vapors into a sensor arrangement to measure the reaction of one or more substance sensing elements located thereinside to the vapors. More particularly, the substance detection device may be configured to selectively operate in at least two modes of operation, comprising a vapor mode, in which the collected sample comprises vapors such that vapor production is not needed, and a trace mode, in which vapors of a collected sample material are produced for analysis. The substance detection device, according to some embodiments, is further configured to rapidly discharge the collected sample and the vapors and clean/decontaminate the sensor arrangement and the sensing elements to allow instant carrying out of further detection cycles.

According to a broad aspect of the present invention there is provided a substance detection device configured and operable to rapidly carry out instant substance detection, followed by a decontamination procedure. In the substance detection cycle, the device collects sample material (e.g., being present either as traces within particles or as discrete particles or vapors or contained in a liquid) from ambient surroundings (e.g., gaseous matter, air) and/or from an inspected item, passes the collected sample material to a chamber comprising a sensor arrangement having a plurality of sensing elements, measures the reaction of the sensing elements to the collected sample material, and determines the presence of one or more specific substances in the collected sample. In the decontamination procedure, the device heats the sensing elements and applies an expelling pressure in said chamber to remove and disengage sample material contained thereinside, and/or that became bound to the sensing elements and/or the internal walls of the chamber. Preferably, each sensing element in the sensor arrangement is configured and operable to react (e.g., chemically) to at least one specific substance and generate data indicative thereof.

The chamber may comprise a one way outlet valve configured and operable to provide passage from the interior of the chamber to an external medium or ambient atmosphere, and to expel sample material/vapors from the chamber and the sensing elements located inside it. In some embodiments the one way outlet valve is configured and operable to open and expel material responsive to a predetermined pressure level inside the chamber. For example, and without being limiting, the decontamination (regeneration) procedure may comprise heating the sensing elements and gradually building positive pressure inside the chamber until the predetermined pressure level is reached inside the chamber. Once the predetermined pressure level is reached inside the chamber, the one way outlet valve opens and the pressure accumulated inside the chamber is instantly released, thereby disengaging substances that became bound to the sensing elements and/or the walls of the chamber during the substance detection period, and expelling it together with sample material/vapors contained inside the chamber therethrough.

The substance detection device may be configured and operable to produce vapors from the collected sample and stream the vapors into the chamber to interact with the sensing elements provided thereinside for measuring the reaction of the sensing elements to the vapors. For example, and without being limiting, the vapors production may be carried out by heating the collected sample immediately after it is collected by the device.

In some embodiments the device is a handheld portable device.

The sensing elements may be arranged inside the chamber in a circular array around an axis, in a linear array spaced apart along a path, or in a combined circular and linear array arrangement. For example, and without being limiting, some sensing elements may be arranged in a circular array and some other sensing elements may be arranged in a linear array. Each sensing element may be configured and operable to react to at least one specific substance, such that the device may be designed to detect a plurality of various different substances in a sample flowing through the device by using a plurality of different sensing elements.

The substance detection device preferably includes an opening (also referred to herein as a sample inlet) for passage of the sample material therethrough to, or from, the chamber, along a sample path defined inside, external or partially external to, the device. The device preferably comprises a pressure unit configured and operable to apply negative (i.e., relative to ambient atmospheric pressure) or positive pressure conditions (pressure profile) inside the chamber. In some embodiments the pressure unit is used for drawing sample material through the opening of the device, along the sample path, and into the chamber, by applying negative pressure conditions inside the chamber. The pressure unit may be further used to apply positive pressure conditions inside the chamber to expel sample/material/vapors contained/bound thereinside.

In some embodiments the sensors are arranged in a linear array spaced apart along said path. Accordingly, a sensing property of the array of sensing elements may be a function of the location of the sensing elements with respect to the sample flow along said path.

In some possible embodiments the chamber comprises a vessel in which the sensing elements are mounted. The vessel is preferably configured and operable to communicate between the sample path and the chamber, such that sample material/vapors passing therethrough contact each one of the sensing elements mounted inside the vessel. For example, and without being limiting, the sensing elements may be arranged inside the vessel in a circular array around a central axis thereof.

The vessel preferably comprises an array of apertures that communicates between the interior of the vessel and the sample path, and between the interior of the vessel and the chamber in which the vessel is contained. For example, and without being limiting, the apertures may be arranged in the vessel in a circular array around its central axis. The apertures are preferably aligned with the circular array of the sensing elements respectively, to thereby provide uniform distribution of the input sample/vapors to the sensing elements.

In some embodiments the vessel includes a plurality of compartments, each capable of accommodating at least one sensing element. Each sensing element may be mounted in its own compartment having apertures communicating it to the sample path and the interior of the chamber. Each compartment thereby defines an environmental region in the vicinity of the sensor element separated from the surroundings of the other compartments. In this configuration, each sensing element is mounted in its own compartment separated from other compartment(s) containing other sensor element(s), respectively.

In some embodiments each compartment comprises at least two apertures configured to communicate between the sample path and the interior of the chamber through the compartment. In this configuration the apertures provided in each compartment provide passage of sample material/vapors through the compartment to/from the chamber, such that the sample material/vapors contact the sensing element(s) mounted inside the compartment while passing through it. For example, and without being limiting, for each compartment, at least one aperture may be provided in an inner wall of a cavity formed in the vessel, and at least one other aperture may be provided in an outer wall of said vessel.

Advantageously, the substance detection device may be powered by a chargeable power source, such as batteries, enclosed inside a housing of the device. Thus, the device may be recharged whenever needed using a suitable battery charger, or alternatively, by replacing used batteries with recharged ones and separately recharging the used batteries. The device in some embodiments is provided with a fastening clip or other attachment means for attaching it to a wearable article of a user (e.g., vest, belt, and/or strap). However, the device may be powered by any other suitable power source (e.g., wireless powering techniques such as employing solar cells and/or magnetic induction), or directly from the electrical grid. The substance sensing elements may generally be of any known type enabling identification of specific substances due to their interaction (chemical reaction) with a sensing material. For example, and without being limiting, a type of piezoelectric crystal element may be used to implement the substance sensing elements, such as described in U.S. Pat. Nos. 6,526,828, 7,159,463 and 7,795,008, of the same applicant hereof.

In some embodiments the sensor arrangement is a removable element in which the substance sensing elements are contained. For example, and without being limiting, the sensor arrangement may be specially designed to permit fast and easy insertion and removal thereof from the substance detection device. The sensor arrangement may comprise one or more sensor compartments in which the sensing elements are securely mounted to prevent inadvertent user contact and damage/breakage of the sensor elements due to shock or vibration.

The substance detection device may be designed to interface with sample collection accessories configured to collect samples from the medium under inspection, (e.g., containers, ambient air, external/internal surfaces of inspected items, fluids), while permitting easy and convenient collection of the samples. The sample collection accessories are preferably configured to permit collection of a sample and/or vapor directly from external and/or internal parts of the inspected medium and rapidly divert the collected sample and/or vapor to the sensor arrangement of the substance detection device for inspection.

For example, and without being limiting, in some embodiments a sample collection accessory configured to connect to an opening of the device is used to collect and heat a stream of air/gas (sample material) and pass it through the opening into the device to contact the heated air stream with the sensing elements. The substance detection device may comprise an electrical connector connectable to the sample collection accessory and usable for powering electrical circuitry (e.g., heating and/or sensing elements) of the sample collection device, and/or for communicating data therebetween. The sample collection accessory may include one or more substance sensing elements configured and operable to react to substances comprised in the collected stream of air/gas and generate measurement data indicative thereof. The substance detection device may be thus configured to receive, through the electrical connector, measurement data from one or more substance sensing elements of the sample collection element and use said measurement data, alone, or in combination with measurement data generated by the substance sensing elements of the sensor arrangement of the substance detection device, to determine the presence of specific substances in the collected sample.

Another accessory, also connectable to the opening of the substance detection device, is usable for collecting samples from surfaces of items by swiping the inspected surfaces with a sample collecting member (swab/fabric/pad) attached to the accessory. Substance detection is then carried out by introducing the sample collection member into the device through the opening and heating it thereinside to produce vapors from the collected sample to be directed towards the sensor arrangement by drawing a stream of air through and/or along the sample collection member and directing the produced vapors to the sensor arrangement to interact with the sensing elements.

In one embodiment, a separate sample collecting unit is used to collect a sample from closed items, such as envelopes and packages, by penetrating (e.g., using a puncturing needle) a hollow tube thereinto through the walls of the inspected item, collecting a stream of air from the interior of the inspected item through and/or along a piece of sample collection member (e.g., swab) attached thereto to collect a sample thereon. The sample collection member may be attached to an accessory capable of connecting to the opening of the device, such that the accessory and the sample collecting member may be removed from the sample collecting unit and connected to the sample inlet (opening) of the device for sample analysis.

In one aspect there is provided a substance detection and identification device comprising a housing, an opening in said housing for passage of sample material therethrough, a sensing unit located in said housing and comprising an array of sensing elements, each configured and operable to interact with sample material in the vicinity thereof for detecting one or more specific substances and generate sensing data indicative thereof, a sample path in the housing between the opening and the sensing unit for facilitating flow of the sample material towards the sensing unit, and a gas inlet assembly in the housing configured for providing a predetermined supply of the sample material to the sensing elements in said array, to thereby enable a predetermined time pattern of the sensing data from the array of sensing elements. A heating unit provided in the housing is configured and operable to heat the sensing elements to thereby physically separate between the sample material and the sensing elements and enable discharge of the sample material by pressure from the sensing unit.

The device comprises, in some embodiments, a control unit configured and operable to receive and process the sensing data generated by the sensing elements and determine the presence of one or more specific substances in the collected sample. In some embodiments a pressure unit located in the housing is used for applying pressure of a certain profile to thereby selectively attract the sample flow along the path into said sensing unit to cause interaction with the sensing elements, and cause the sample flow from the sensing elements to discharge the sample from the housing.

In some embodiments the sensing unit comprises the sensing elements arranged in a circular array around an axis, where the sample path connects the opening and a location on said axis. The sensing unit comprises, in some embodiments, a vessel containing the circular array of sensing elements, formed with an array of apertures arranged around the axis and being aligned with the array of the sensing elements respectively. In this configuration the apertures serve as the gas inlets for the sample passage towards the respective sensing elements, resulting in a substantially concurrent supply of the sample to the sensing elements, and also serve as gas outlets for flow of the separated sample from the sensing elements.

In some embodiments the sensing unit comprises the sensing elements arranged in a linear array along the sample path. Such a linear array may, for example, be used in addition to circular array(s). For example, two or more circular arrays may be arranged at different locations along the sample flowing path.

In some possible embodiments the sensing unit is mounted in a chamber. The chamber may be configured for removably mounting the sensing unit thereinside. Optionally, the heating unit and the housing are configured for removably mounting the heating unit in the housing in the vicinity of the sensing unit. In addition, the heating unit may be configured with a geometry matching that of an arrangement of the sensing elements in the sensing unit.

The chamber may comprise a one way outlet valve configured and operable to permit discharge of the sample from the chamber. For example, and without being limiting, the one way outlet valve may be configured and operable to respond to a predetermined pressure level inside the chamber for selectively shifting from its normally closed state to an open state to permit discharge of the sample from the chamber.

In some possible embodiments the heating unit is configured and operable to receive the sample material drawn through the opening in the housing and produce vapors thereof. For example, and without being limiting, the heating unit may comprise a first heater configured and operable for heating the sensing elements to physically separate between the sample and the sensing elements, and a second heater for producing the vapor of the received sample. Each of the sensing elements in the device may be accommodated in a dedicated compartment of the sensing unit defining the vicinity of the sensing element, the compartment being formed with the gas inlets and outlets for passage of the sample into and out of the compartment.

In some possible embodiments the opening in the housing is configured to sealably connect to a sample collection accessory. Accordingly, the pressure unit may be operable for drawing the sample from the sample collection accessory through the opening. The sample collection accessory is configured in some embodiments to draw a stream of ambient air with the sample therethrough. The sample collection accessory may comprise a handheld unit having a handle at a proximate portion thereof and a sample collector at a distal portion thereof, where the sample collector is configured for adsorbing a sample material thereon and for connection to the opening of the housing.

In some embodiments the substance detection device is configured and operable to establish electrical connection with the sample collection accessory when connected to the opening. A controller may be used in the device to identify the electrical connection with the sample collection accessory and operate the heating unit (e.g., to produce vapors of the collected sample).

In another aspect there is provided a kit for use in detection of foreign substances, the kit comprising a handheld portable substance detection device configured as described hereinabove or hereinbelow, wherein the housing has an opening configured to sealably connect to one or more predetermined sample collection accessories, thereby enabling to receive a sample flow therefrom by pressure, and a set of the one or more sample collection accessories each configured to collect sample material from the vicinity thereof and, when connected to the housing, deliver the collected sample through the opening.

In some possible embodiments the kit comprises a handheld portable substance detection device having a housing containing a sensing unit configured and operable to interact with sample material in the vicinity thereof for detecting one or more specific substances, and generate sensing data indicative thereof, where the housing of the device has an opening configured to sealably connect to one or more predetermined sample collection accessories, to thereby receive a sample flow from the connected sample collection accessory to the sensing unit, and a set of the one or more sample collection accessories each configured to collect sample material from the vicinity thereof and, when connected to the housing of the device, to deliver the collected sample through the opening.

The kit may further comprise a wearable article (e.g., vest or belt) configured and operable to conveniently access various elements of the kit and allow quick utilization thereof. For example, and without being limiting, the kit may comprise a vest having one or more pockets, pouches or holders, designed to receive, and releasably hold, the handheld portable substance detection device and/or the handheld sample collecting unit, and one or more sample collection accessories associated with them.

The set of one or more sample collection accessories may comprise a sample collection accessory configured to draw a stream of ambient air with the sample therethrough. The substance detection device may be therefore configured and operable to establish electrical connection with the sample collection accessory being connected to the opening of the device. For example, and without being limiting, the substance detection device may comprise a controller configured and operable to identify the electrical connection with the sample collection accessory and operate an internal heating element of the sample collection accessory to produce vapors of the collected sample.

The one or more sample collection accessories may comprise the sample collection accessory configured as a handheld unit having a handle at a proximate portion thereof and a sample collector at a distal portion thereof, the sample collector being configured for adsorbing a sample material thereon, and for connection to the opening of the housing. For example, and without being limiting, the sample collection accessory may be configured for removably attaching the handle of one or more different sizes to the proximate portion thereof, thereby enabling replacement of the handle. The kit may thus comprise a set of handles of different sizes.

In some possible embodiments the kit comprises a set of sample collection accessories for drawing ambient air with the sample therethrough, where the sample collection accessories of the set differ from one another in at least a length thereof. The kit may further comprise a belt fastening arrangement configured for comfortably carrying the substance detection device and for fastening it to a belt worn by the user. A charger may be also comprised in the kit for charging a rechargeable power source of the substance detection device.

In some possible embodiments the kit comprises a handheld unit configured for collecting a sample from a vicinity thereof by suction, and comprising a slot for receiving a sample collector portion of the sample collection accessory, thereby enabling absorbance of the sample collected by the handheld unit onto the sample collector portion, where the sample collector is configured for connecting to the opening of the housing. For example, and without being limiting, the handheld unit may have a handle at a proximate portion thereof, a tube at a distal end thereof, and contain a vacuum pump for suction of the sample through the tube towards said slot.

The handheld unit may be configured for removably attaching one of the tubes of different sizes to the distal end thereof, to thereby enable replacement of the tube. For example, and without being limiting, the kit may comprise a set of the tubes of different sizes.

In yet another aspect there is provided a sample collecting unit for collecting a sample from a vicinity thereof. The sample collecting unit is configured as a handheld unit, and comprises a housing, a handle connectable to the housing at one side thereof, and a tube connectable to the housing at an opposite side thereof, wherein the housing contains a vacuum pump for suction of a sample from surroundings through the tube, and the housing has a slot for receiving a sample collector portion of a separate sample collection accessory, thereby enabling absorbance of the sample flowing through the tube onto the sample collector portion.

In yet another inventive aspect of the present invention there is provided a substance detection and identification device comprising a housing having front and rear sides, a sensing unit comprising an array of sensing elements including a certain number of spaced-apart rows of sensing elements (e.g., linear arrays) mounted inside the housing, each sensing element configured and operable to interact with sample material in the vicinity thereof for detecting one or more specific substances and generating sensing data indicative thereof, a certain number of inlet openings formed in the front side of the housing for passage of sample material therethrough into the housing, each of the inlet openings being associated with one row of sensing elements of the array, and a pressure unit (e.g., pump, blower/mini-blower) device mounted in the rear side of the housing and configured and operable to draw a certain number of fluid streams (e.g., of ambient air) into the housing, each fluid stream being drawn through a respective one of the inlet openings for interaction with the sensing elements of a respective row in the array.

In some embodiments the rows of the sensor array are configured as separate modules allowing for easy and quick replacement of any one of the rows-module of sensing elements of the array. In this way the substance detection and identification device may be quickly adapted for detection of different types of materials by replacing one or more replaceable rows/modules of sensing elements of the array with other replaceable sensing elements/rows carrying particular types of sensing elements for detection and identification of particular substances. Accordingly, the substance detection and identification device may be quickly adapted for various different applications (e.g., wine testing, explosive detection, narcotic detection), by replacing one or more of the rows of sensing elements of the array.

Optionally, and in some embodiments preferably, at least some of the inlet openings have different sizes to thereby affect different flow rates of at least some of the fluid streams. The location of each inlet opening (e.g., a center of the opening) on the front side of the housing optionally corresponds to a location of sensory portions of the sensing elements in the respective row associated with the inlet opening.

The device may comprise a control unit configured and operable to actuate the pressure unit and the sensing elements, and receive and process the sensing data generated by the sensing elements responsive to the fluid streams drawn into the housing. In some embodiments the device comprises a communication module (e.g., adapted for wireless data or Bluetooth® communication) configured and operable to receive data associated with the sensing data from the control unit and transmit the same to a local or remote computer system (e.g., a smart mobile device, a desktop computer, a laptop, or a remote/local server).

In yet another aspect of the present invention there is provided a monitoring system comprising a plurality of the substance detection and identification devices having said control unit and said communication module, the local or remote computer system configured and operable to receive and process the data transmitted from the one or more substance detection devices and generate corresponding indications, and a data storage system for storing the measurement data from the plurality of substance detection and identification devices.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings, like reference numerals are used to indicate corresponding parts, in which:

FIGS. 1A and 1B schematically illustrate a handheld portable substance detection device according to some possible embodiments, wherein FIG. 1A is a front perspective view of the device, and FIG. 1B is an exploded back perspective view showing a belt attachment arrangement of the device;

FIGS. 3A to 3I schematically illustrate a sample analysis assembly according to some possible embodiments, wherein FIG. 3A is an exploded perspective view of the sample inspection assembly, FIG. 3B is a perspective view of a sensor arrangement of the assembly, FIGS. 3C and 3D, respectively, are bottom and elevated perspective views of a sensor matrix of the sensor arrangement, FIGS. 3E to 3G, respectively, are elevated, bottom, and sectional, perspective views of a sensor chamber of the sensor arrangement, and FIGS. 3H and 3I, respectively, are elevated and sectional perspective views showing a vapor production and collection unit of the sample inspection assembly;

FIGS. 5A to 5C schematically illustrate an accessory for collection and production of vapors from ambient air, according to some possible embodiments, wherein FIG. 5A is a perspective view demonstrating interfacing the vapors production and collection accessory to the substance detection device, FIG. 5B is an exploded perspective view of the vapors production and collection accessory, and FIG. 5C is a perspective view of a sample collection nose;

FIG. 6B is an exploded perspective view showing elements of the sample collection accessory, FIGS. 6C and 6D demonstrate setting the sample collection accessory to collect a sample utilizing an extension wand, and FIGS. 6E and 6F exemplify a two part sample collection accessory having a quick connection assembly;

FIGS. 8A to 8C schematically illustrate a substance inspection accessory having internal sensing and vapor extraction elements, wherein FIG. 8A shows connection of the substance inspection accessory to the substance detection device, FIG. 8B shows a sectional view of the substance inspection accessory, and FIG. 8C shows an exploded view of the substance inspection accessory;

FIG. 9 is a flow chart demonstrating a measurement cycle of the substance detection device according to some possible embodiments;

FIG. 10C is a block diagram exemplifying possible use of the miniature substance detection device.

DETAILED DESCRIPTION OF EMBODIMENTS

Figure 1A:
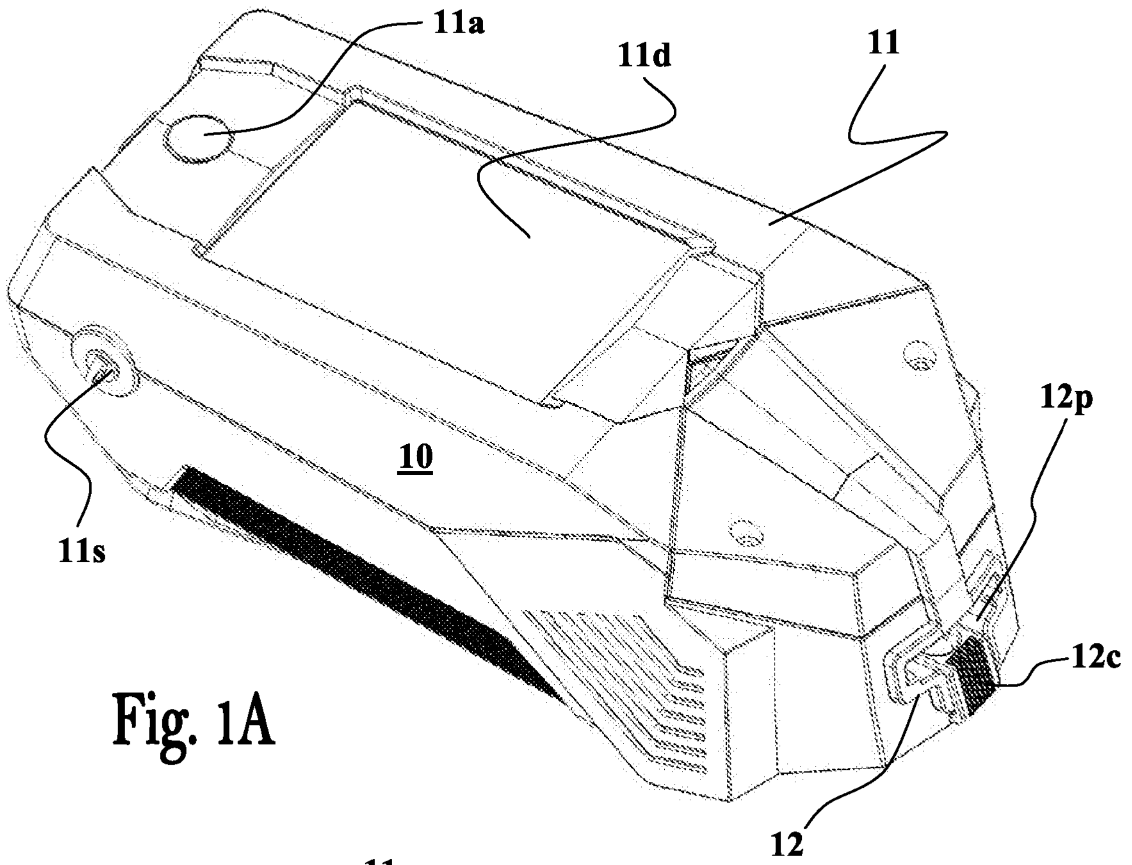

The various embodiments of the present invention are described below with reference to the drawings, which are to be considered in all aspects as illustrative only and not restrictive in any manner. Elements illustrated in the drawings are not necessarily to scale, emphasis instead being placed upon clearly illustrating the principles of the invention. This invention may be provided in other specific forms and embodiments without departing from the essential characteristics described herein.

The present invention provides a handheld portable device and interfacing accessories for collecting an examined sample, producing vapors from the collected sample and bringing the produced vapors to interact with an arrangement of sensors to determine the presence or absence of one or more substances in the examined sample. The substance detection device of the present invention may be configured and operable to collect and examine a sample of ambient air, produce vapors from the collected sample and flow the produced vapors towards the sensor arrangement to interact with substance sensing elements thereof, each of said substance sensing elements being configured and operable to react to minute quantities of a specific substance. In some embodiments the sensor arrangement comprises a sensor chamber comprising one or more substance sensing elements, and the vapors flow into the sensor chamber for carrying out the substance detection.

In some embodiments the substance detection device is configured to interface with sample collection accessories usable for collecting sample material from external surfaces of objects (e.g., bags, luggage, purses, garments, cars, trucks, airplanes, air cargo and maritime containers, and suchlike), or from interiors/cavities of hollow items (e.g., receptacles, envelopes, suitcases, and suchlike), onto a sample collection member.

The substance detection device is configured to receive a portion of the sample collection accessory containing the sample collection member, produce vapors from sample material collected by the sample collection member and draw the produced vapors into the sensor chamber of the sensor arrangement to determine the presence/absence of said one or more specific substances in the collected sample.

FIG. 1A is an elevated perspective view of a substance detection device 10 according to some possible embodiments. The substance detection device 10 comprises a housing 11 enclosing a sample inspection assembly (20 in FIGS. 2 and 3A) and various components for operating the sample inspection assembly, a display device 11*d* (e.g., LCD), an activation button 11*a*, and a sample inlet 12. The sample inlet 12 comprises an opening 12*p* configured and operable to collect a sample of ambient air from the surrounding environment. The sample inlet 12 is also configured to interface with a sample collection accessory to receive a sample material for substance inspection. Although the device 10 shown in FIG. 1A comprises a single activation button 11*a*, it is clear that additional press buttons may be added if so needed. Additionally or alternatively, the display device 11*d* may be a type of touch screen configured and operable to interact with a user operating the device by displaying information and receiving user's inputs via displayed objects (e.g., touch buttons, list-boxes, sliders, and the like).

Figure 1B:
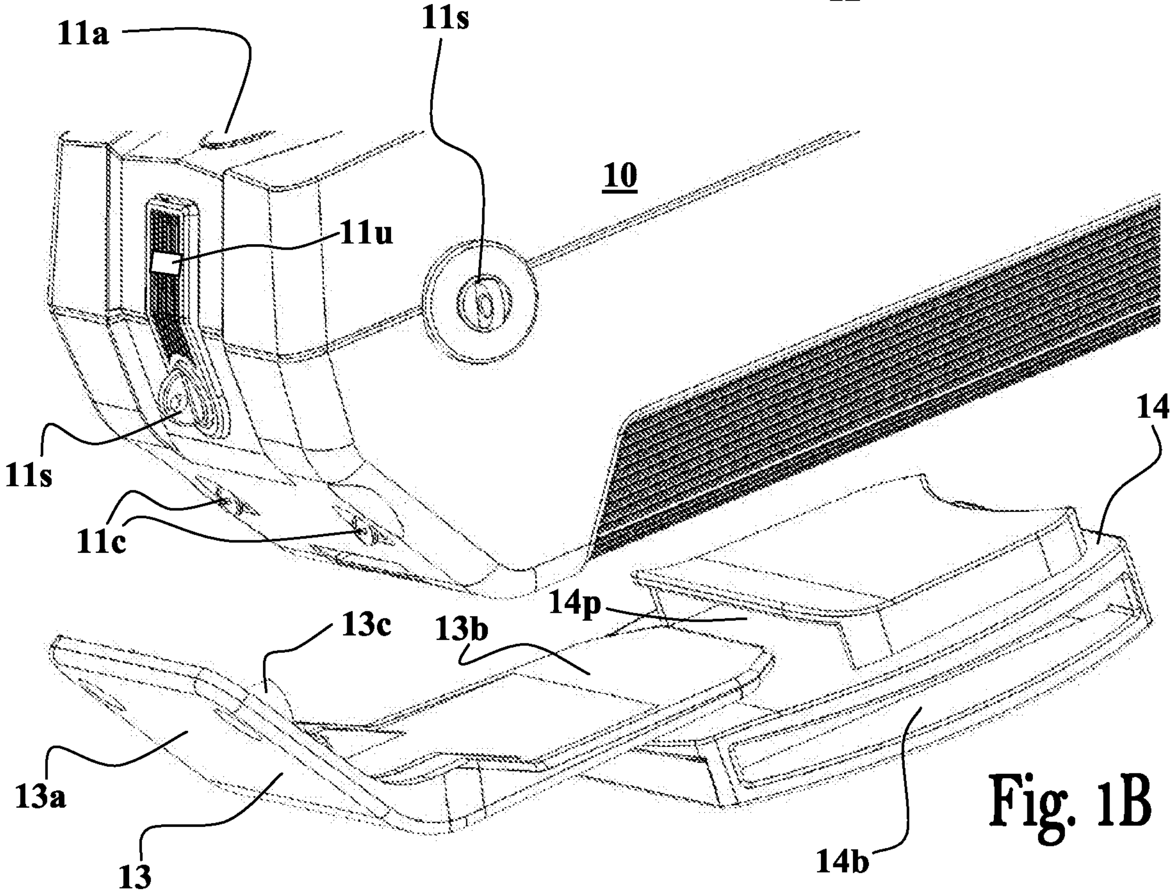

The housing 11 of the substance detection device 10 may further comprise various attachment means, such as strap fasteners 11*s*. With reference to FIG. 1B, the housing 11 may be further configured to connect to a belt attachment arrangement 14. For this purpose a clip 13 may be connected by an attachment plate 13*a* to the housing 11 (e.g., via screws 11*c*), where the clip 13 comprises a tongue portion 13*b* configured to be received in a socket 14*p* of the belt attachment arrangement 14. The belt attachment arrangement 14 may further comprise a belt pass-through slot 14*b* configured to attach to a belt passed therethrough. The device 10 may further comprise a data port 11*u* (e.g., Micro and Mini USB) to provide connectivity to external computer systems for data exchange (e.g., substance detection results), software/firmware updates, and/or calibration.

The substance detection device may be compactly designed to provide a handheld portable device having geometrical size/dimensions that enable a comfortable hand grip of the device by a user (e.g., similar to the size of a handheld flashlight, PDA, Smartphone, and suchlike) and easy operation thereof.

Figure 2:
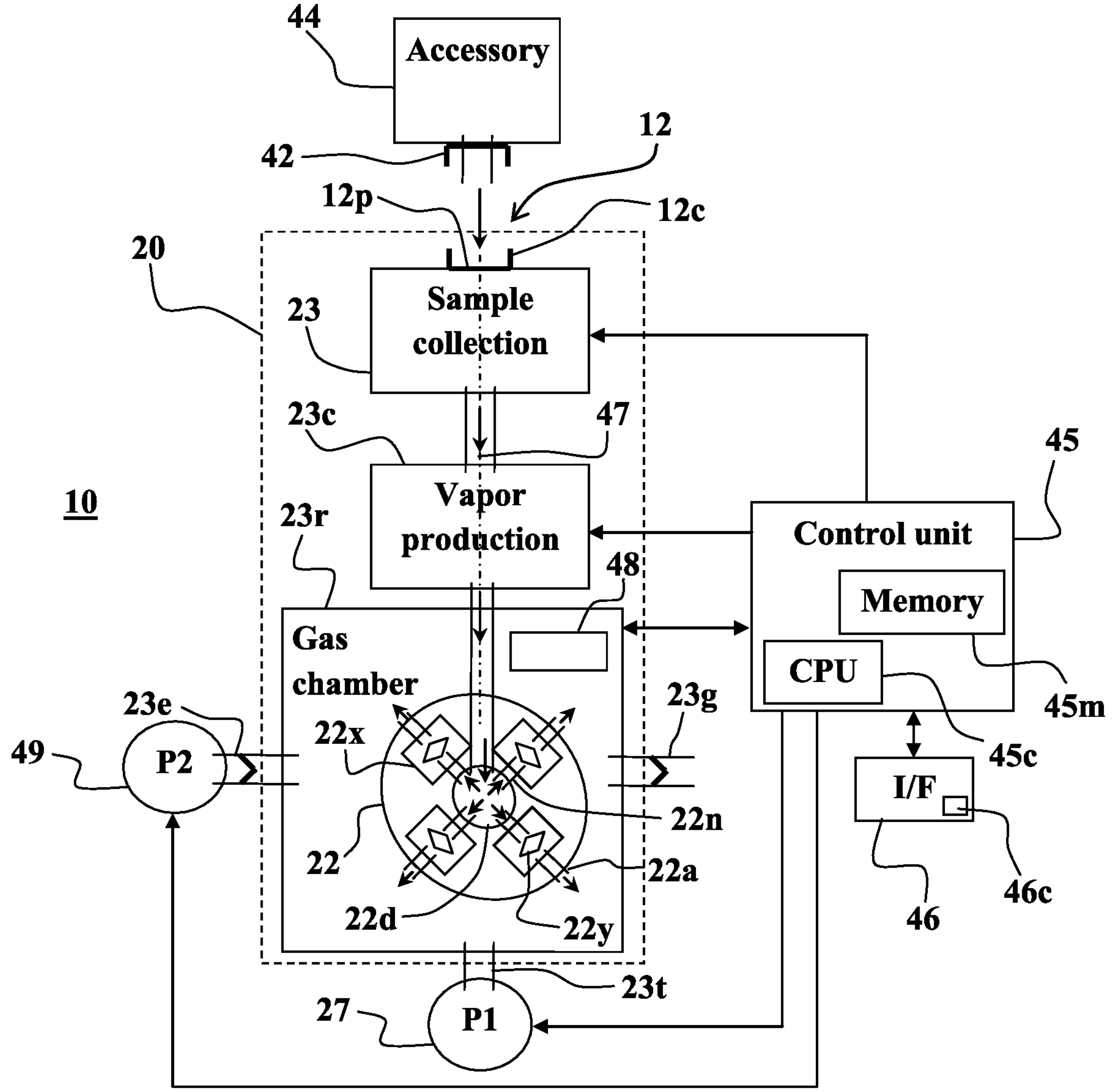
FIG. 2 is a block diagram showing functional blocks of a substance detection device according to some possible embodiments.

FIG. 2 is a block diagram illustrating functional blocks of a substance detection device 10 according to some possible embodiments. The device 10 generally comprises a sample inspection assembly 20 configured and operable to collect/receive sample material/vapors and determine the presence of specific substances therein, an air pump 27 connected to the sample inspection assembly 20 through a suction/injection port 23*t*, and a control unit 45. The control unit 45 is configured and operable to operate functional units of device 10, measure the reaction of substance sensing elements 22*y* located in the sample inspection assembly 20 to the sample material/vapors, and determine the presence or absence of specific materials in the sample accordingly. The control unit 45 may thus comprise a processor 45*c* and a memory 45*m*, and it may be coupled to a user interface unit 46 configured and operable to receive user inputs and to output data related to the device operational state and to results of substance detection cycles carried out by the device 10. The user interface unit 46 may further comprise one or more data communication interfaces and/or connectors (e.g., USB) 46*c* for exchanging data (over wires/cables or wirelessly) with external devices (e.g., personal computers, PDAs, Smartphones, IT Servers, Command and Control Centers and suchlike).

The sample inspection assembly 20 comprises, in some embodiments, a sample collecting unit 23 configured and operable to collect sample material/vapors for inspection, a vapor production unit 23*c* configured and operable to produce vapors from the collected sample, a gas chamber 23*r* configured and operable to draw the vapors into a sensor arrangement 22 to thereby cause substance sensing elements 22*y* positioned thereinside to interact with the sample material/vapors. The sensor arrangement 22 is configured and operable to permit sample transfer between the interior of the gas chamber 23*r* and sensor compartments 22*x* provided therein, in which the substance sensing elements 22*y* are situated, via a first set of (outer) apertures 22*a*. The sensor compartments 22*x* and the vapor production unit 23*c* are configured to permit sample transfer therebetween via a separate second set of (inner) apertures 22*n*, and the vapor production unit 23*c* and the sample collection unit 23 are also configured to permit sample transfer between them.

This configuration thus provides a sample passage path 47 along which sample material is passed into the device, vapors are produced from the collected sample material, and the produced vapors flow into the sensor compartments 22*x* of the sensor arrangement 22. In some possible embodiments the sample collection 23 and vapor production 23*c* unit are combined into a single unit that receives the sample material and produce therefrom the vapors which flow into the sensor compartments 22*y* of the sensor arrangement 22.

For example, and without being limiting, a substance detection cycle of the device 10 may be initiated by the control unit 45 responsive to user input received through the interface unit 46. In response, the control unit 45 activates the air pump 27 to apply through the suction/injection port 23*t* negative pressure conditions (i.e., vacuum) inside the gas chamber 23*r* to thereby cause sample collection through the sample collection unit 23. The control unit may concurrently activate the vapor production unit 23*c* to produce vapors from the collected sample material. The negative pressure conditions applied inside the gas chamber 23*r* are communicated through the sensors compartments 22*y*, the vapor production unit 23*c* and the sample collection unit 23 to a sample inlet 12 of the sample collection unit 23, and thereby cause suction of ambient air into the device 10 via the opening 12*p* of the sample collection unit 23.

Due to negative pressure conditions inside the chamber 23*r* sample material is drawn into the vapor production unit 23*c*, in which vapors are produced from the sample material, and the produced vapors are drawn from the vapor production unit 23*c* into the gas chamber 23*r* and uniformly distributed into the sensor compartments 22*y* via the inner apertures 22*n*. The sample material/vapors thus pass through the sensor compartments 22*x* and thereby interact with the sensing elements 22*y* mounted inside them. The reaction of the sensing elements 22*y* to the vapors is measured and measurement data indicative thereof is generated. The control unit 45 then processes and analyzes the measurement data and determines the presence of specific materials in the sample material.

The gas chamber 23*r* comprises, in this example, an inlet port 23*e* and an outlet port 23*g* configured and operable to facilitate discharge/expelling of the sample/vapors from the gas chamber 23*r*, and cleaning/decontamination of the substance sensing elements 22*y* from traces thereof. For this purpose one or more heating devices 48 may be provided in the gas chamber 23*r* to heat the substance sensing elements 22*y* to thereby disengage substance particles that became bound to the substance sensing elements 22*y* during the substance detection cycle. To facilitate sample discharge and disengagement, the outlet port 23*g* may comprise a one way valve configured to permit passage therethrough only from the interior of the gas chamber 23*r* to the external environment (the atmosphere), and the outlet port 23*e* may comprise a one way valve configured to permit passage therethrough only from the external environment into the interior of the gas chamber 23*r*. An additional pump 49 may be connected to the gas chamber 23*r* via the inlet port 23*e* to facilitate discharge of the sample/vapors from the gas chamber during the sensor cleaning/decontamination procedure.

The sample discharge and decontamination (regeneration) procedure is preferably performed by the control unit 45 as follows: the heating device(s) 48 is activated to heat the substance sensing elements 22*y* and the air pump 27 is activated to apply a positive pressure pulse inside the gas chamber 23*r* to discharge the sample material/vapors via the fluid outlet port 23*g* and the opening 12*p* (i.e., along the sample collection path 47); the additional pump 49 is then activated to gradually build positive pressure conditions inside the gas chamber 23*r* until a predetermined pressure level is reached thereinside; upon reaching the predetermined pressure level the one way valve in the outlet port 23*g* opens and the pressure in it is instantly released through the outlet port 23*g* to the external environment, thereby disengaging and expelling sample/vapor from the sensing elements 22*y*. The control unit 45 then deactivates the heating device(s) 48 and the additional pump 49, and waits to receive user input from the user interface 46 for commencing a new detection cycle.

During the discharge and decontamination stages, the inner apertures 22*n* and the outer apertures 22*a* serve for the flow of clean gas (air or inert agent) through the respective compartments 22*x*. The dimensions and shape of the compartments 22*x*, as well as those of their apertures, are selected so as to meet aerodynamic requirements, consisting of providing proper operation of the sensing elements (e.g., natural oscillations of piezoelectric quartz crystal resonators), building the needed negative or positive pressure conditions inside the chamber, and a desired speed of the sample therethrough. The inventors of the present invention found that the use of separate compartments 22*x* provides better sensitivity, selectivity and specificity of the substance analyzed.

The sensor arrangement exemplified in FIG. 2 includes four sensor compartments 22*x* housing four sensing elements 22*y* in them respectively. It is however noted that the sensor arrangement of the substance detection device 10 may be configured to contain more, or less, than four sensing elements. For example and without being limiting, in some possible embodiments the sensor arrangement is configured to contain 8, 16 or 64, sensing elements (or any number in between), or optionally two or a single sensing element.

FIG. 2 also demonstrates use of an interfacing accessory device 44 usable according to some possible embodiments for collection of sample material/vapors. The accessory device 44 may be configured and operable to collect the sample from ambient air, inspected surfaces or inner cavities/volumes of inspected items, and communicate the sample and/or its vapors to the sample inspection assembly 20 via the sample inlet 12 of the sample collection unit 23. In some embodiments the accessory device 44 is also configured to establish electrical connection with device 10 through a connector 12*c* provided in, or near, the sample inlet 12. An electrical connector 42 provided in the accessory device 44 is used to establish the electrical connection.

The control unit 45 may be thus configured and operable to identify connection of the accessory device 44 to the device 10 once the electrical connection is established therebetween via the electrical connectors 42 and 12*c*, and, whenever needed, pass electric signals thereover to the accessory device 44 to carry out sample collection via the accessory device 44.

Figure 3A:
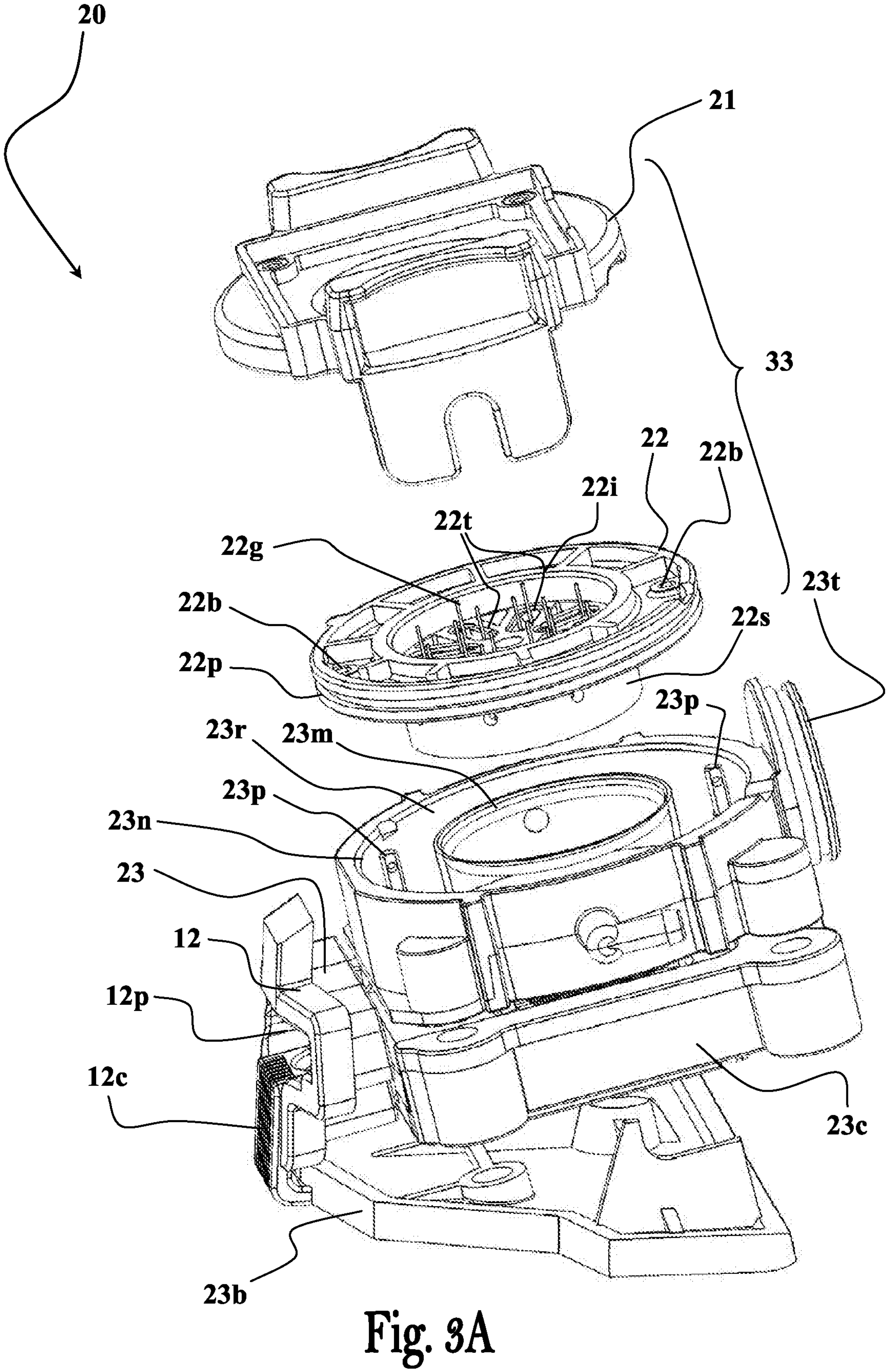

FIG. 3A is an exploded perspective view of a sample analysis assembly 20 of the substance detection device 10 according to some possible embodiments. In this example the sample analysis assembly 20 comprises the sample inlet 12 and a sample collection (23) and vapor production (23*c*) units attached to a base member 23*b*, a gas chamber 23*r*, a sensor arrangement 22 (also referred to herein as a vessel), and a sensor matrix 21. The sensor matrix 21 is configured and operable to receive and retain a sensor interfacing portion 22*i* of the sensor arrangement 22 at a bottom portion thereof, provide connectivity and interface to electrical terminals 22*g* of substance sensing elements of the sensor arrangement 22 for connecting a printed circuit board (PCB, 29 in FIG. 4) thereto. The sensor matrix 21 is further configured to seal the sensor interfacing portion 22*i* (e.g., by O-rings) so as to prevent gas passage from a sensor chamber 22*s* of the sensor arrangement 22 via its upper openings 22*t*.

Figure 3B:
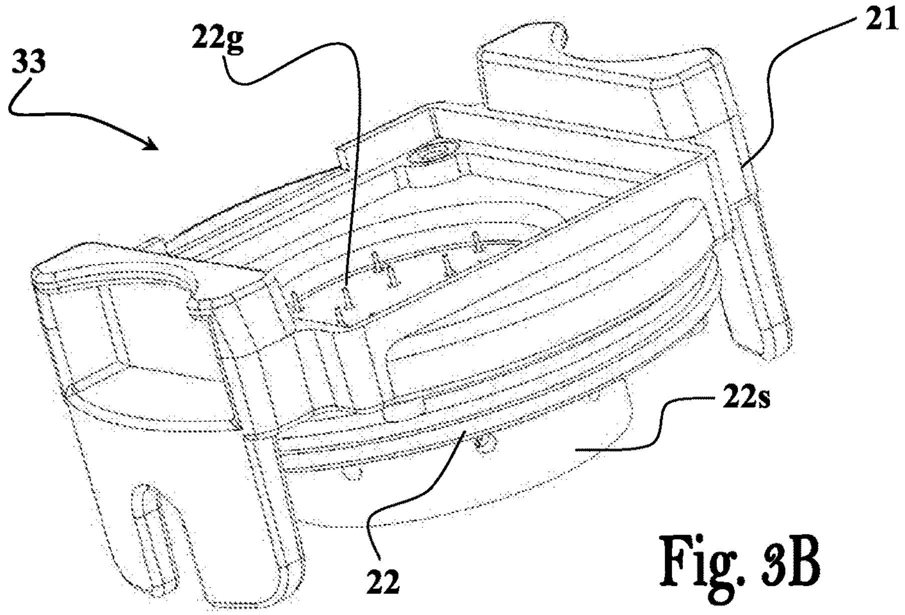
Figure 3C:
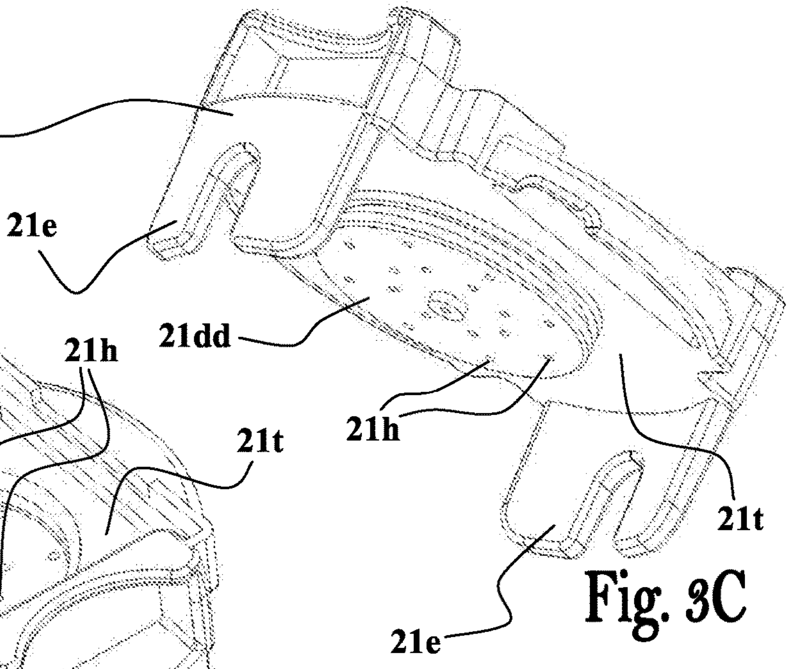
Figure 3D:
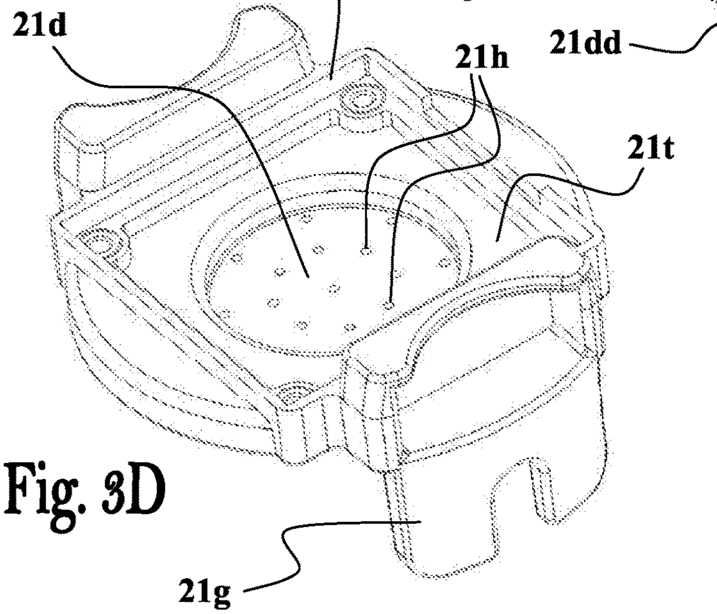

As exemplified in FIG. 3B, the sensor arrangement 22 is sealably attached to the bottom side of the sensor matrix 21 to form a removable sensor assembly 33 providing electrical connectivity to the sensors' terminals 22*g*. With reference to FIGS. 3C and 3D, the sensor matrix 21 comprises a tray portion 21*t* having a plurality of terminal pass-through bores 21*h* formed in a sunken surface 21*d* thereof. Two lateral legs 21*e* are attached vertically to the tray portion 21*t* for supporting the sensor arrangement 22 when positioned inside the gas chamber 23*r*. The sunken surface 21*d* is configured to form a downwardly protruding (e.g., circular) surface 21*dd* at the bottom part of the sensor matrix 21, said downwardly protruding surface 21*dd* being shaped to provide connection to the sensor arrangement 22.

Figure 3E:
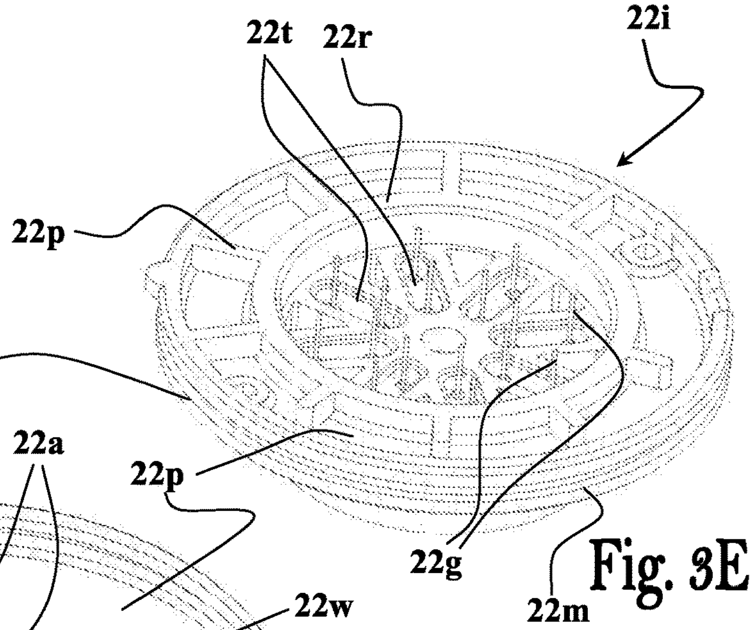

With reference to FIG. 3E, the interfacing portion 22*i* of the sensor arrangement 22 is formed on a plate portion 22*p* comprising a fitting 22*r* (e.g., circular upwardly protruding rim) configured to mate with the downwardly protruding surface 21*dd* of the sensor matrix 21. In this way, the sensor arrangement 22 can be attached to the sensor matrix 21 by passing the sensor terminals 22*g* through the pass-through bores 21*h* of the sunken surface 21*d* and mating the fitting 22*r* in the interfacing portion 22*i* of the sensor arrangement 22 over the downwardly protruding surface 21*dd* of the sensor matrix 21.

Figure 3F:
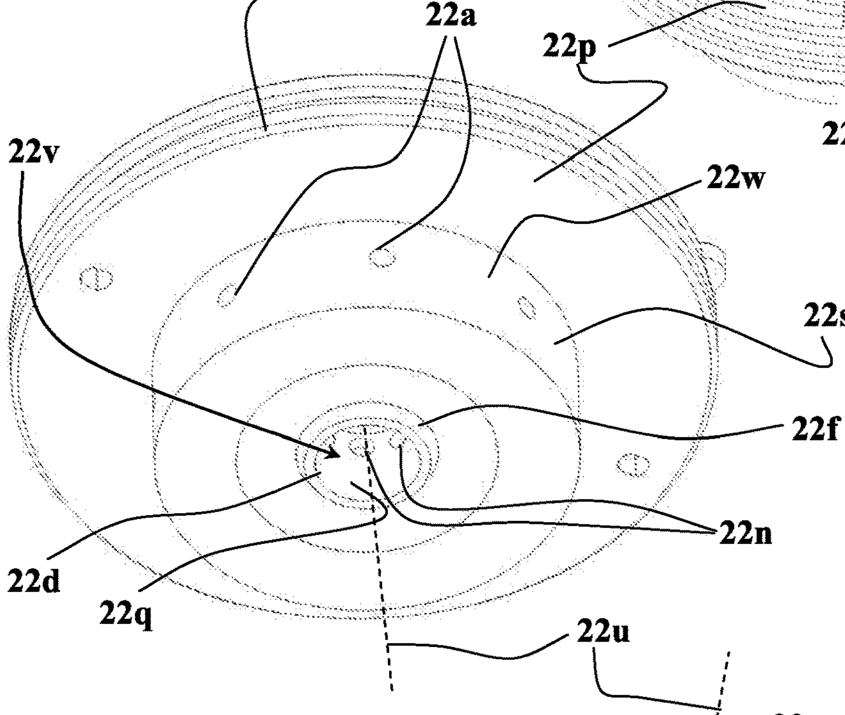

As seen in FIG. 3F the sensors' chamber 22*s* protrudes downwardly from the bottom surface of the plate portion 22*p* of the sensor arrangement 22. The sensors chamber 22*s* comprises an outer wall 22*w* substantially perpendicular to the plate portion 22*p*, and a central cavity 22*v* having an inner wall 22*q* accessible from below via an opening 22*d*. The outer wall 22*w* comprises a plurality of outer apertures 22*a* arranged in a circular array around a central axis 22*u* of the sensors chamber 22*s* to provide passage for sample material to/from the internal sensor compartment (22*x* in FIG. 3G) of the sensors chamber 22*s* via said outer apertures 22*a*, and a respective plurality of inner apertures 22*n* arranged in the inner wall 22*q* in a circular array around the central axis 22*u* to provide passage for sample material to/from the internal sensor compartment of the sensor chamber 22*s* via the bottom opening 22*d*.

As illustrated in FIG. 3A, the sensor assembly 33 is configured to be removably received in the gas chamber 23*r* via an opening 23*n* thereof and retained thereinside e.g., by means of bores 22*b* provided in the sensor arrangement 22 configured to be received over respective posts 23*p* provided in gas chamber 23*r*. The rim 22*m* of the plate portion 22*p* of the sensor arrangement 22 is configured and operable to securely fit inside the opening 23*n* of the gas chamber 23*r* and sealably close the opening 23*n* when the sensor assembly 33 is positioned thereinside. A holder member 23*m* (e.g., supporting ring) may be provided inside the gas chamber 23*r* configured and operable to receive and hold the sensor chamber 22*s* inside the gas chamber 23*r*. The holder member 23*m* may be elevated above the inner surface of the gas chamber 23*r* to thereby retain the sensor chamber 22*s* over a portion of the outer wall 22*w* located above the outer apertures 22*a* without blocking gas passage through them.

Figure 3G:
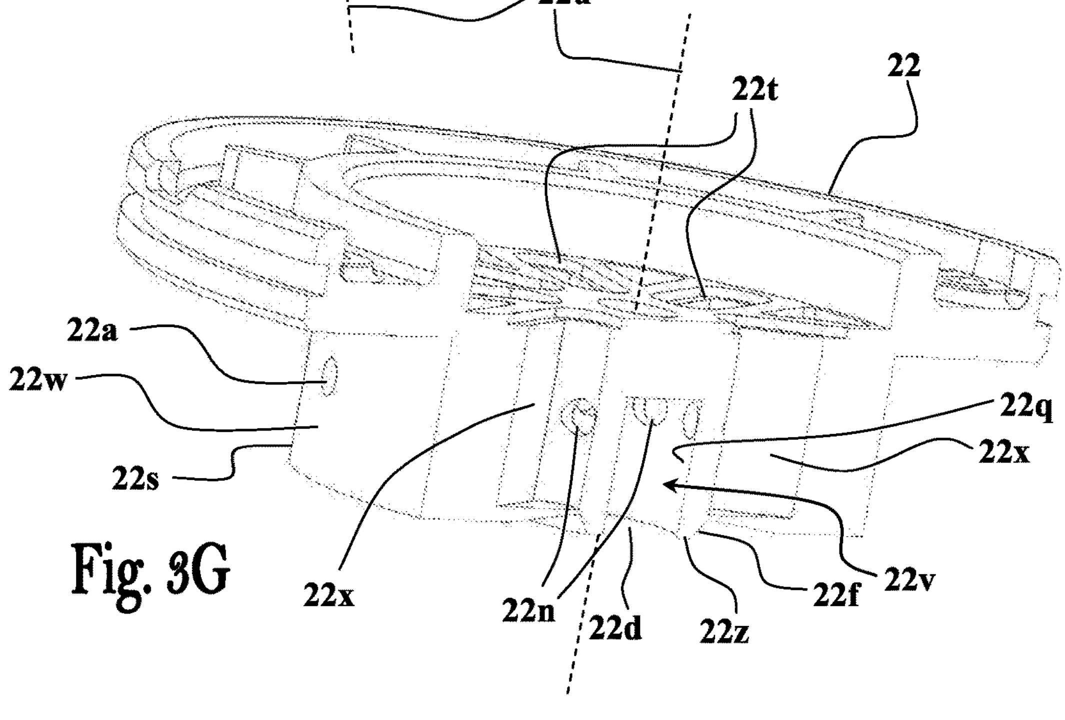

The substance sensing elements (not shown) of the sensor arrangement 22 are located inside the sensor compartments 22*x* shown in the sectional view of FIG. 3G. In some embodiments the sensor chamber 22 is a circular element having a central cavity 22*v* having the sensor compartments 22*x* uniformly distributed around the central axis 22*u* of the chamber 22. Each sensor chamber 22*x* has an upper opening 22*t* through which the terminals of the substance sensing element project upwardly. As seen in FIG. 3E, the upper openings 22*t* may be sealed by the substance sensing element, and/or by dedicated seal members. As best seen in FIG. 3G the interior of each one of the sensor chambers 22*x* is accessible via at least two apertures, an outer aperture 22*a* provided in the outer wall 22*w* of the sensor chamber 22 to communicate between the interior of the gas chamber 23*r* and the sensor chamber 22*x*, and an inner aperture 22*n* provided in the inner wall 22*q* of the sensor assembly 22 to communicate between the central cavity 22*v* and the sensor chamber 22*x*.

Figure 3H:
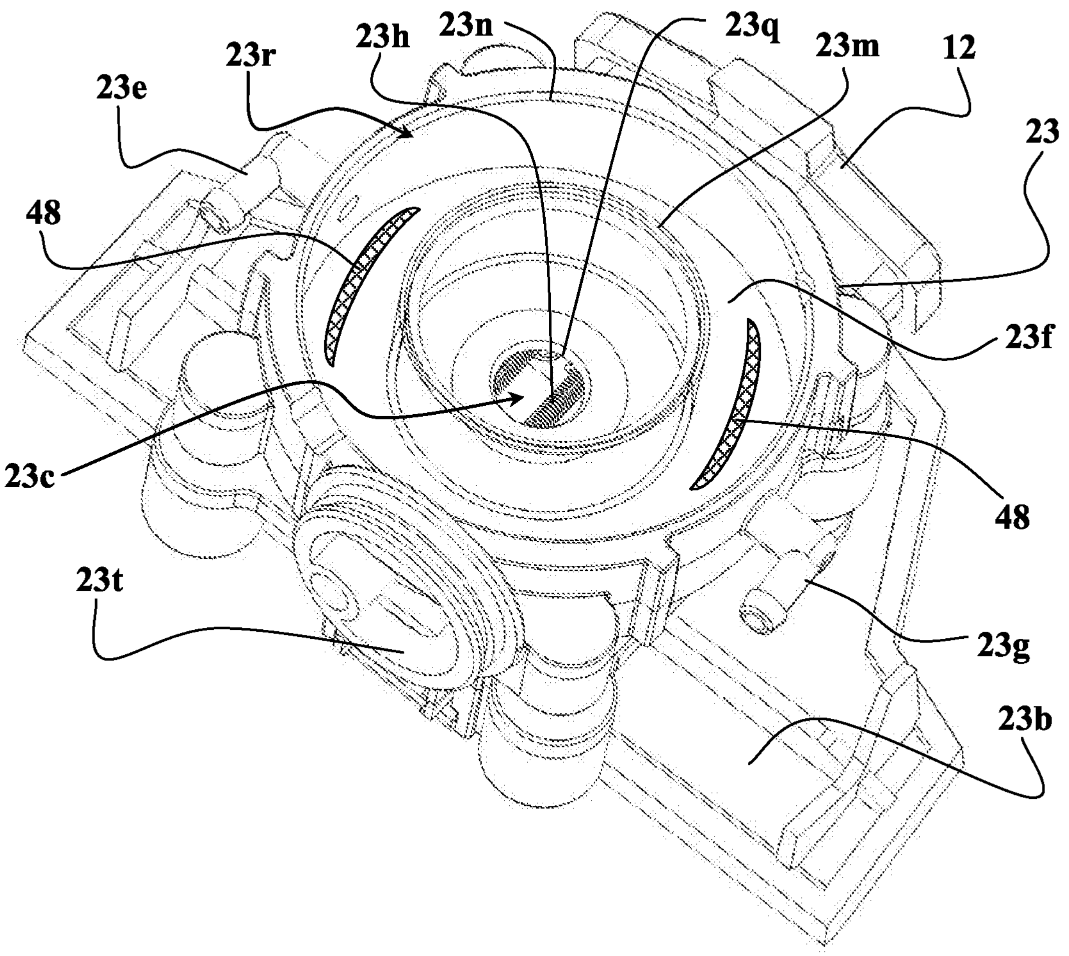

As seen in FIG. 3G, the inner wall 22*q* of the sensor chamber 22 comprises a rim 22*z* protruding and tapering downwardly. With reference to FIG. 3H, the rim 22*z* of the sensor chamber is configured to be sealably received inside a sample port 23*q* provided in the bottom surface 23*f* of the gas chamber 23*r*. The sample port 23*q* facilitates communication between the interior of the gas chamber 23*r* and the interiors of the sample collection unit 23 and the vapor production unit 23*c* wherein heating elements 23*h* are placed for heating samples collected for substance detection. The gas chamber 23*r* comprises the inlet port 23*e* and the outlet port 23*g*, the function and structure of which have been described hereinabove with reference to FIG. 2, and a suction/injection port 23*t* configured and operable to connect the gas chamber 23*r* to the air pump 27 for applying negative or positive pressure conditions inside the chamber 23*r*. For example, and without being limiting, the air pump 27 may be operated to draw a stream of air/gas into the gas chamber 23*r* via the sample collection unit 23 (i.e., along the path 47) by applying negative pressure conditions (suction) inside the gas chamber 23*r*. The air pump 27 may be operated to expel a stream of gas/air from the gas chamber 23*r* (through the outlet port 23*g* and the sample path 47) by applying positive pressure conditions inside the gas chamber 23*r* (i.e., by facilitating flow of a stream of gas/air into the gas chamber 23*r*).

More particularly, communication of the inlet/outlet ports 23*e*/23*g* to the atmosphere (ambient) air is facilitated via one way valves (not shown) configured to permit passage therethrough in one direction. For example, and without being limiting, the outlet port 23*g* may be configured to permit flow only from the interior of the gas chamber 23*r* to the atmosphere and prevent entry of gas/air into the gas chamber 23*r*, while the inlet port 23*e* may be configured to permit passage therethrough only from the atmosphere into the interior of the gas chamber 23*r*. In this way the gas chamber 23*r* is maintained substantially sealed and air/gas may be driven/drawn through it by applying negative or positive pressure conditions thereinside via the suction/injection port 23*t*.

Figure 3I:
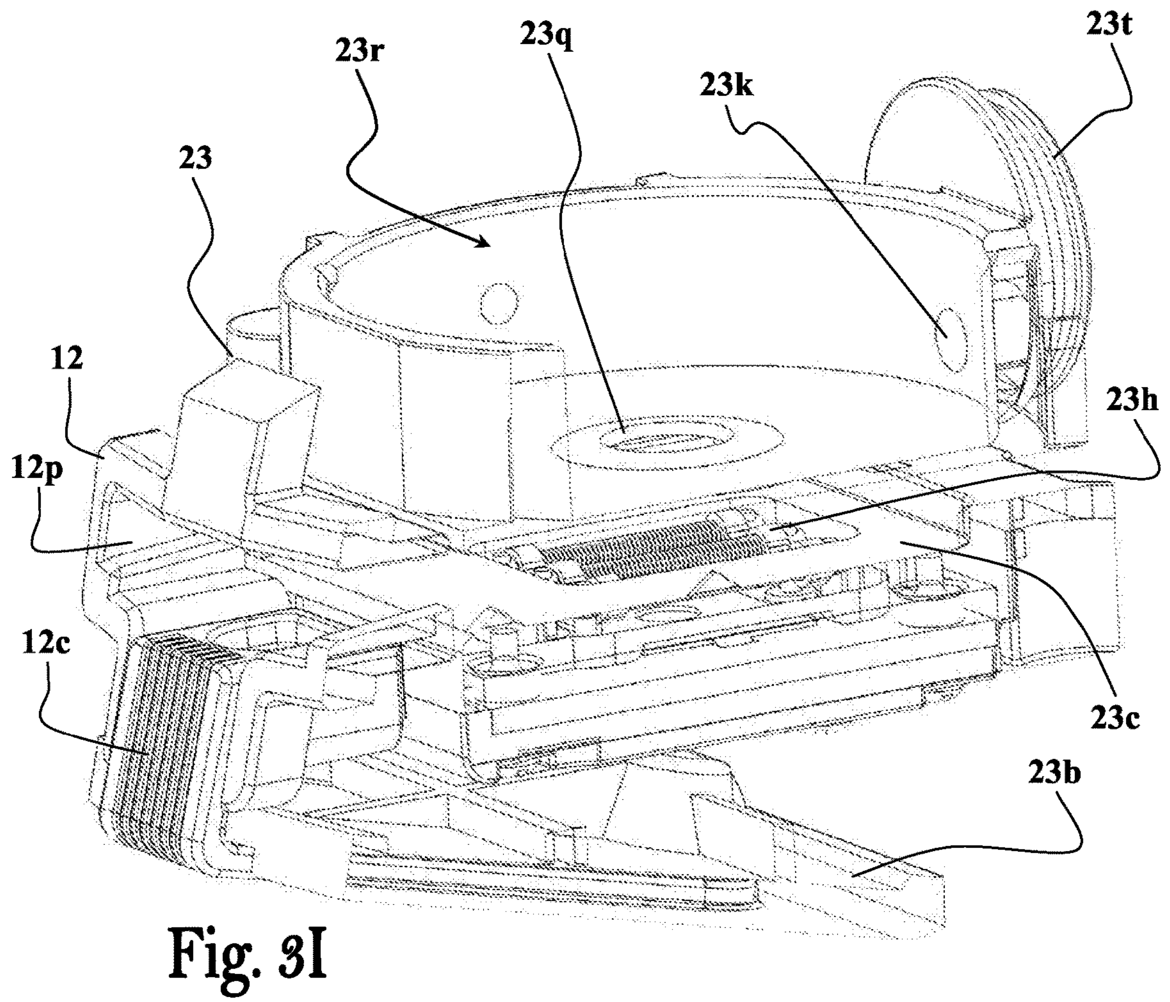
Figure 4:
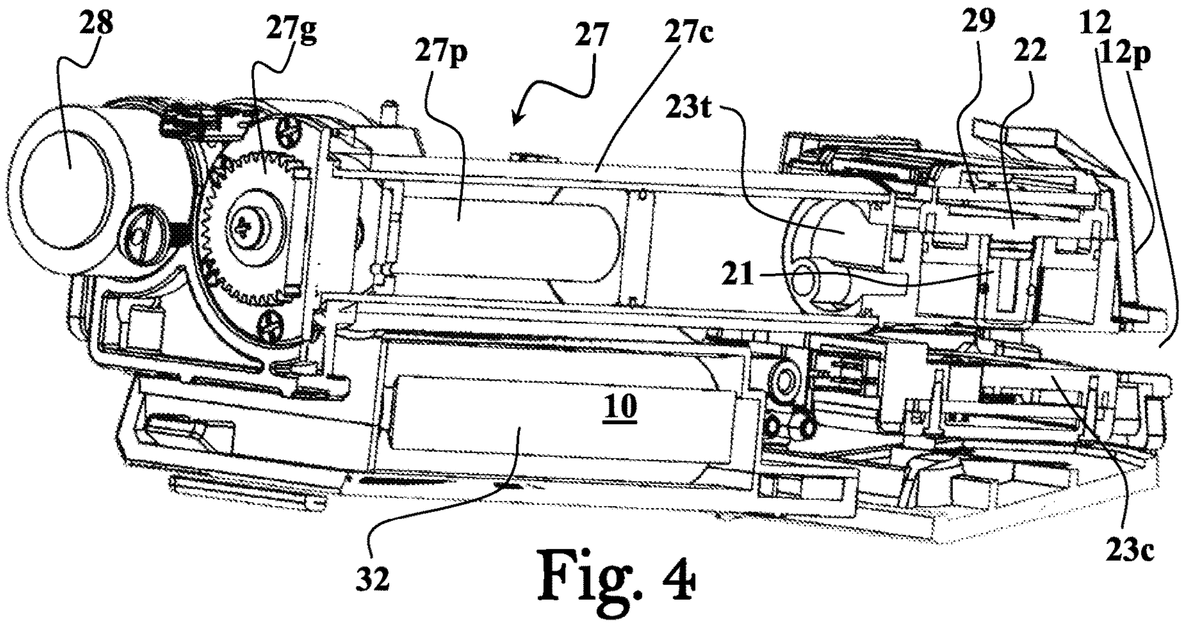
FIG. 4 is a longitudinal section perspective view of the device without its housing.

The gas chamber may further comprise one or more heating devices 48 configured and operable to heat the sensor arrangement 22 during decontamination procedures carried out after (or before) substance detection cycles. FIG. 3H exemplifies an embodiment in which two heating devices 48 are used, but of course other embodiments are possible employing a single heating device 48, or more than two such heating devices 48. During the decontamination procedure the heating devices 48 heat the sensing elements 22*y* situated inside the sensor arrangement 22 to facilitate disengagement of substance particles that became bound to the sensing elements 22*y*. FIG. 4 shows a sectional view of the substance detection device 10 according to some possible embodiments. As seen, the suction/injection port 23*t* is connected to air pump 27 configured and operable to controllably draw or suck air/gas through the suction/injection port 23*t*. For example, the air pump 27 may be implemented by a cylinder 27*c* and piston 27*p* assembly configured and operable to inject air into the gas chamber by drawing the piston distally towards the suction/injection port 23*t*, or to suck air/gas from the gas chamber by drawing the piston 27*p* proximally away from the suction/injection port 23*t*. A gear system 27*g* may be used to transfer rotary motion from an electric engine (not shown) powered by batteries 32, and translate it into linear axial motion for moving the piston 27*p* along the interior of the cylinder 27*c*. With reference to FIG. 3I, a detection cycle of the substance detection device 10 may be activated by pressing the activation button 11*a* which initiates a sequence of operations for sampling and inspecting a stream of ambient air. The detection cycle may be initiated by heating the heating element 23*h* and thereafter performing sample suction by drawing the piston 27*p* proximally. The air pump 27 communicates with the gas chamber via a hole 23*k* connecting the interior of the gas chamber to the suction/injection port 23*t* to which the air pump is connected. Thus, as the piston 27*p* is drawn away from the suction/injection port 23*t* negative pressure conditions evolve inside the gas chamber 23*r* causing suction of ambient air through the opening 12*p* of the sample inlet 12. A stream of ambient air is thus drawn into the sample collection (23) and vapor production unit 23*c* wherein it is heated by the heating element 23*h* and vapors produced therefrom are drawn through the sample entry port 23*q* into the gas chamber 23*r*. Referring now to FIGS. 3F to 3H, the vapors entering the gas chamber 23*r* through the sample port 23*q* are drawn through the bottom opening 22*d* into the central cavity 22*v* of the sensor chamber 22*s*, and therefrom drawn into the sensor compartments 22*x* through the inner apertures 22*n*. The streamed sample passes through the sensor compartments 22*x* and comes into contact with the sensing elements mounted inside them. The reaction of the substance sensing elements (22*y*) to the vapors is then measured and measurement data indicative of the reaction of the sensing elements to the sample material/vapors is generated and processed to determine presence of one or more specific materials.

Figure 5A:
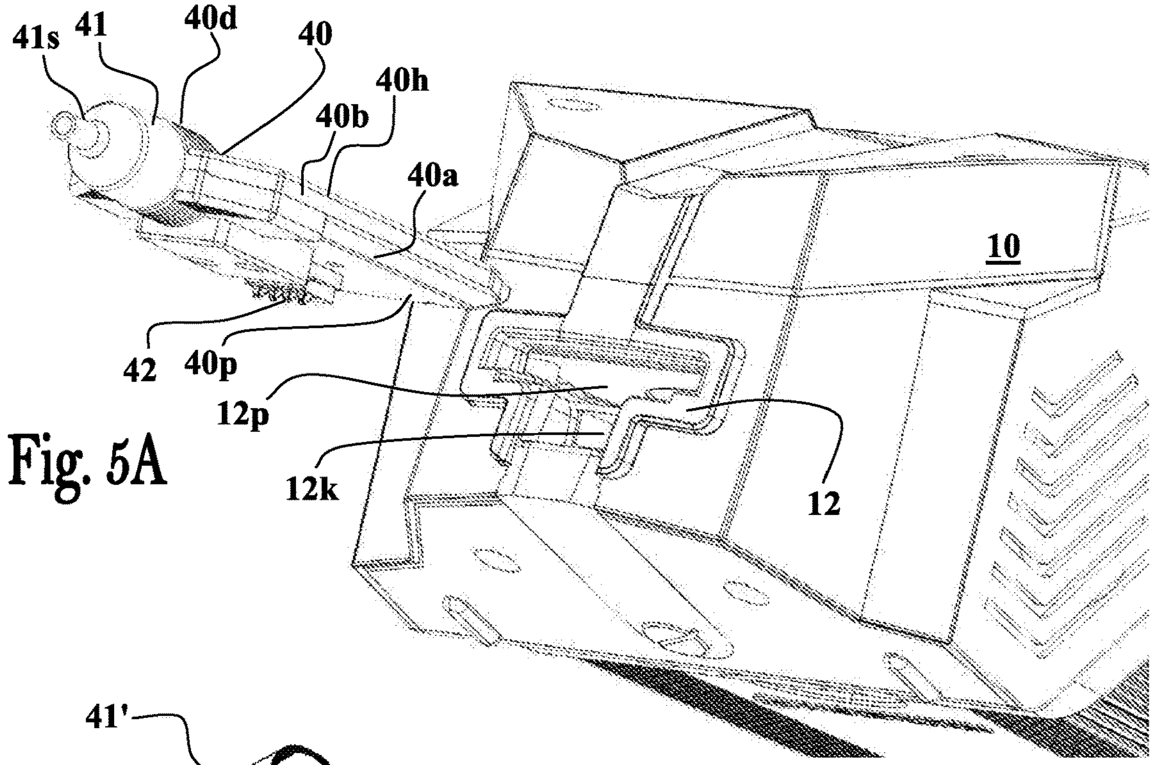

FIG. 5A illustrates a possible embodiment employing a sample collecting accessory 40 connectable to the sample inlet 12 of the substance detection device 10. The sample collecting accessory 40 has a proximal end 40*p*, a distal end 40*d*, and a substantially flat housing structure 40*h* extending therebetween. A portion of the proximal end 40*p* of the sample collecting accessory 40 is configured and operable to be received via the opening 12*p* of the sample inlet 12 to thereby communicate between the interior of the sample collecting accessory 40 and the sample inspection assembly 20 via a hole (40*r* in FIG. 5B) provided on one face of the accessory 40. The distal end 40*d* of the sample collecting accessory 40 comprises a nose element 41 configured and operable to facilitate sample collection from hollow items (e.g., bottles, receptacles, and suchlike). For this purpose a narrow tube 41*s* (e.g., having an inner diameter of about 2 to 3 mm) may be provided at the end of the nose element 41 to enable accessing cavities and hollow parts via slender passages of such inspected items. The device 10 having the sample collecting accessory 40 connected to its sample inlet 12 may be operated as described hereinabove to inject a stream of ambient air into the sample inspection assembly 20 through the sample collecting accessory 40 by introducing the narrow tube 41*s* of the nose element 41 into a cavity or hollow part of an inspected item and drawing a sample material therefrom for inspection.

The sample collecting accessory 40 may comprise an electrical connector 42 attached to its housing 40*h* and configured and operable to mate and establish electrical connection with a respective connector element 12*k* provided inside the device 10.

Figure 5C:
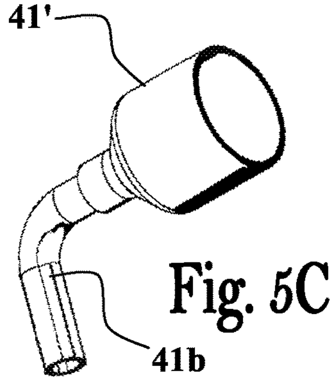
Figure 5B:
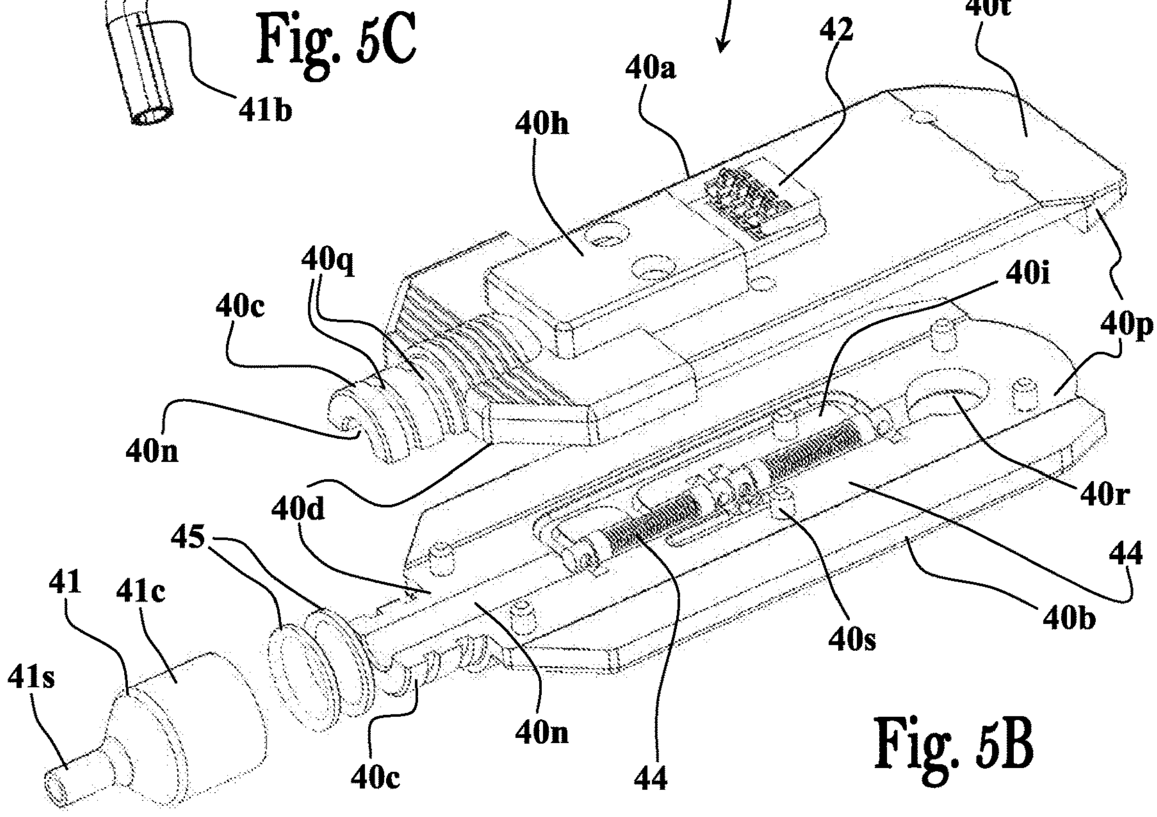

With reference to FIG. 5B, the housing 40*h* of the sample collecting accessory 40 may be assembled from two relatively flat pieces 40*a* and 40*b* (e.g., connected by pins 40*s* and respective sockets), configured to form a taper 40*t* at a proximal end portion of the housing and a cylindrical structure 40*c* at the distal end 40*d* of the housing. The inner sides of the pieces 40*a* and 40*b* of the housing 40*h* are configured to form an inner channel 40*n* along a distal section of the housing and an elongated cavity 40*i* along a middle section of the housing, in which heating elements 44 are situated. The inner channel 40*n* passes along the cylindrical structure 40*c* and the hole 40*r* formed in a proximal section of the piece 40*b* of the housing 40*h* is connected to the elongated cavity 40*i*, thereby forming a continuous sample path extending between the distal end 40*d* and the hole 40*r*. A cup structure 41*c* of the nose element 41 is configured and operable to attach to the cylindrical structure 40*c* of the housing and seal it (e.g., using O-rings 45), to thereby allow suction of air via the narrow tube 41*s* of the nose element 41 and through the inner channel 40*n* into the elongated cavity 40*i* of the sample collection accessory 40.

The heating elements 44 of the sample collection accessory 40 are electrically connected to the connector 42 such that they may be activated by the control unit (45) to heat a stream of air passing through the accessory 40, when the accessory 40 is connected to the sample inlet 12 of the device 10. A 'trace mode' detection cycle employing the sample collection accessory 40 may thus comprise connecting the accessory 40 to the sample inlet 12 powering the heating elements 44 and activating the air pump 27 to apply negative pressure conditions inside the gas chamber 23*r* and thereby cause suction of air through the nose element 41 into the accessory 40. The air drawn into the accessory 40 passes through the inner channel 40*n* into the elongated cavity 40*i* wherein it is heated by the heating elements 44 to produce vapors thereof.

The produced vapors are drawn through the hole 40*r* into the sample inspection assembly 20 wherein they are inspected to determine presence of specific substances, as described hereinabove.

In some possible embodiments the 'trace mode' detection cycle comprises heating the collected sample using the heating elements 44 of the accessory 40 and the heating elements 23*h* of the vapors production unit 23*c*. The control unit 45 may be thus configured, or receive user instructions as to whether to activate only the heating elements 44 of the accessory 40, only the heating elements 23*h* of the vapors production unit 23*c*, or simultaneously activate both heating elements 44 and 23*h*.

The accessory 40 may be also used for carrying out a 'vapor mode' detection cycle when connected to the sample inlet 12 of the device 10, wherein the accessory is used to directly collect vapors of a substance (e.g., by introducing the narrow tube 41*s* of the nose element 41 into a receptacle comprising a liquid material), thus not requiring activation of any of the heating elements. It is however noted that in some applications one or more heating elements may be activated in the 'vapor mode' detection cycles to further produce vapors and prevent condensation of the vapors during their passage towards the sensor arrangement 22.

FIG. 5C demonstrates a nose element 41' having a narrow tube 41*b* which is angled to facilitate the access of the nose element 41' into cavities and hollow spaces of inspected articles. In this example the angle of the narrow tube 41*b* is substantially a right angle, but of course any other suitable angles (or curved configurations) may be used. The nose element of the sample collecting accessory 40 is thus designed to be readily replaceable to adjust thereto a nose element suitable for accessing a cavity/hollow space of an inspected item. To further facilitate its accessibility into cavities, narrow tube (41*b* or 41*s*) may be made from a flexible or elastic material to thereby allow twisting and bending it through curved passages and cavities of inspected items.

Figure 6A:
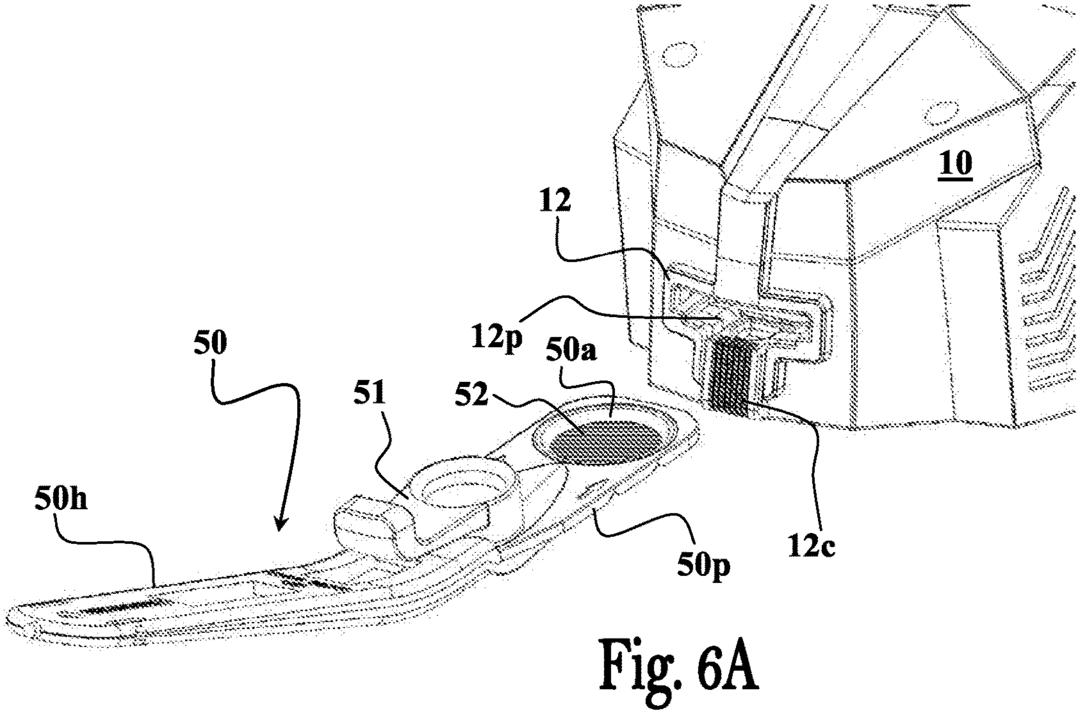
FIGS. 6A to 6F schematically illustrate a sample collection accessory usable for collecting samples by rubbing an examined surface, wherein FIG. 6A demonstrates interfacing the sample collection accessory with the substance detection device.

FIG. 6A demonstrates use of a handheld sample collection accessory 50 usable for introducing collected sample material into the sample inspection assembly 20 of the device 10. The sample collection accessory 50 is a handheld device comprising a handle 50*h* and a sample collection portion 50*p* extending from the handle 50*h*. A sample collecting member 52 is attached inside a hole 50*a* formed near a distal end of the sample collection portion 50*p*. After sample material is collected with the sample collecting accessory 50, its sample collection portion 50*p* is introduced via the opening 12*p* of the sample inlet 12 into the sample inspection assembly 20 such that the sample collecting member 52 is situated inside the vapors production unit 23*c*. In this state a detection cycle of device 10 may be commenced by activating the heating elements 23*h* of the vapor production unit 23*c* to produce vapors from the sample material collected by the sample collection member 52 and operating the air pump 27 to draw the vapors into the gas chambers 23*r* for inspection by the sensing elements.

Figure 6B:
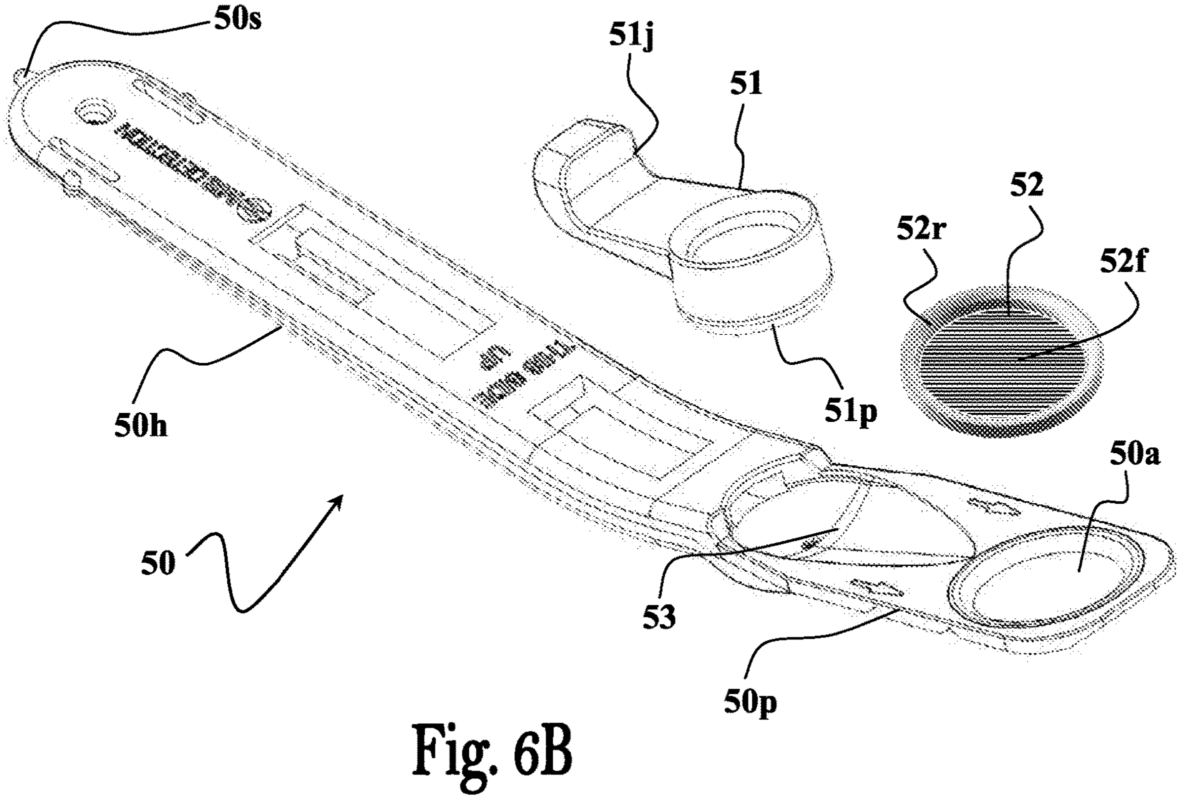

Referring to FIG. 6B, in some embodiments the sample collecting member 52 comprises a piece of flexible/elastic absorbent/porous material 52*f* (e.g., made of Nomex®, Sontara® or any other suitable material) fixedly attached to a ring member 52*r*. Preferably, the sample collecting member 52 and the ring member 52*r* are fixedly attached to the hole 50*a* in the sample collection portion 50*p* of the accessory 50. The sample collecting accessory 50 also comprises a plug 51 comprising at one end thereof a grip 51*j* and at its other end an impress 51*p* configured and operable to be received in the hole 50*a* over the sample collecting member 52. The impress 51*p* is configured to reversibly attach to the ring member 52*r* and press the sample collecting member 52 downwardly to form a bump 52*b* therewith, as illustrated in FIG. 6D. In this state sample material may be collected by pressing the bump 52*b* onto an inspected surface and rubbing/swiping it therewith. After sample material is collected the plug 51 may be removed from the hole 50*a* and the sample collecting member 52 may be introduced into the sample inspection assembly 20 through the opening 12*p* for vapor production and inspection, as described hereinabove.

Figure 6C:
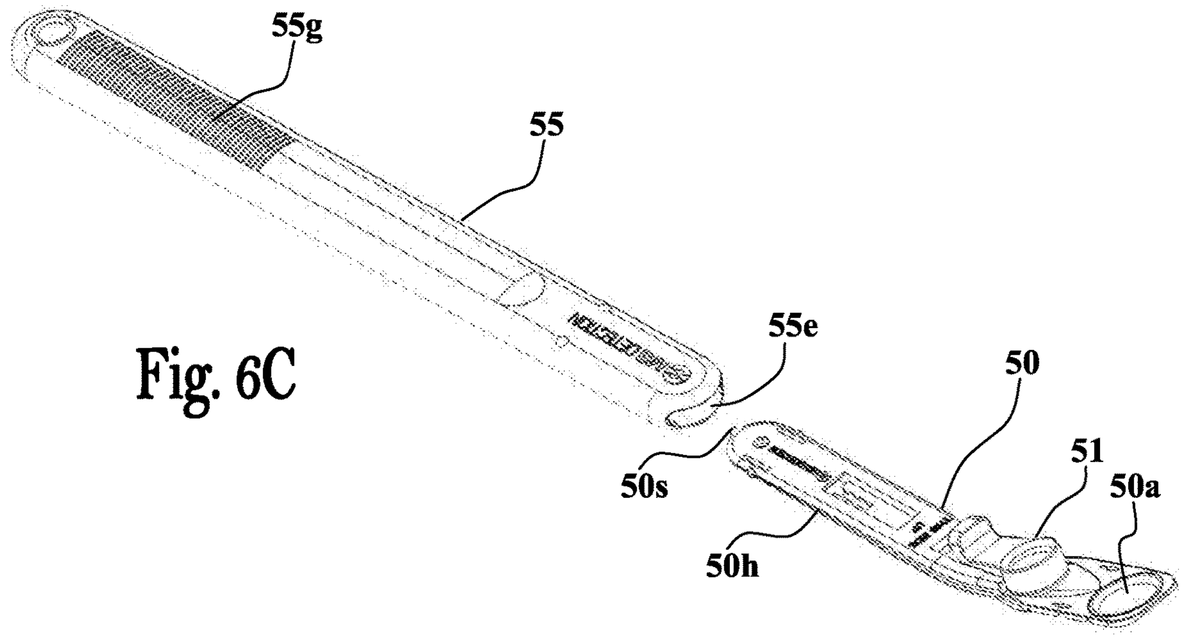
Figure 6D:
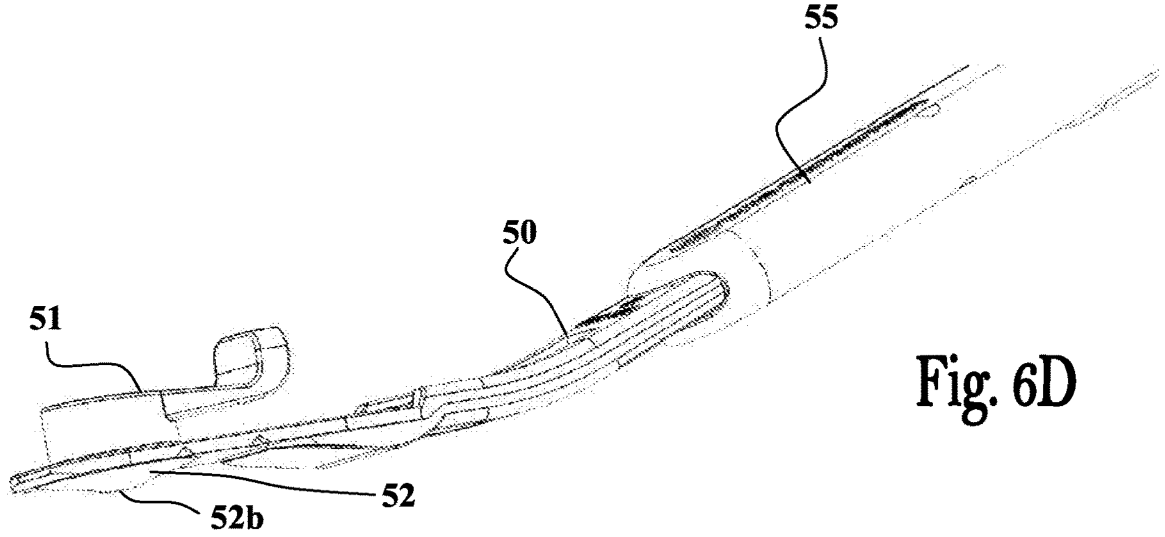

After collecting the sample material the plug 51 may be attached in a retaining slot 53 formed in the sample collecting accessory 50, as illustrated in FIG. 6C. With reference to FIG. 6B, the handle 50*h* of the sample collecting accessory 50 may comprise a stylus tip 50*s* usable for operating the display 11*d* of the device 10 when implemented with a touch screen. Referring to FIGS. 6C and 6D, an extension 55 may be connected to the handle 50*h* of the sample collecting accessory 50 to facilitate the sample collection performed therewith. As demonstrated in FIG. 6C, a proximal end portion of the handle 50*h* of the sample collecting accessory 50 may be introduced into a socket 55*e* formed at a distal end of the extension 55, and held thereinside to thereby allow the user to grip the formed assembly via a handle portion 55*g* at the other end of the extension 55.

Figure 6E:
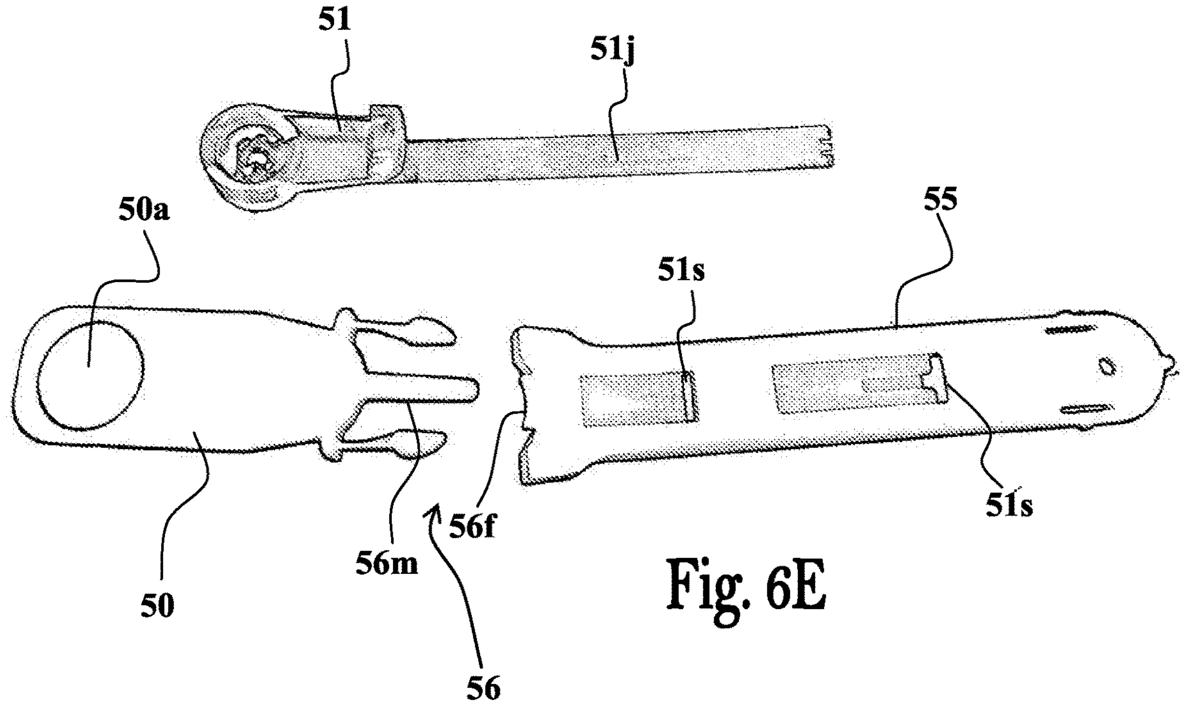
Figure 6F:
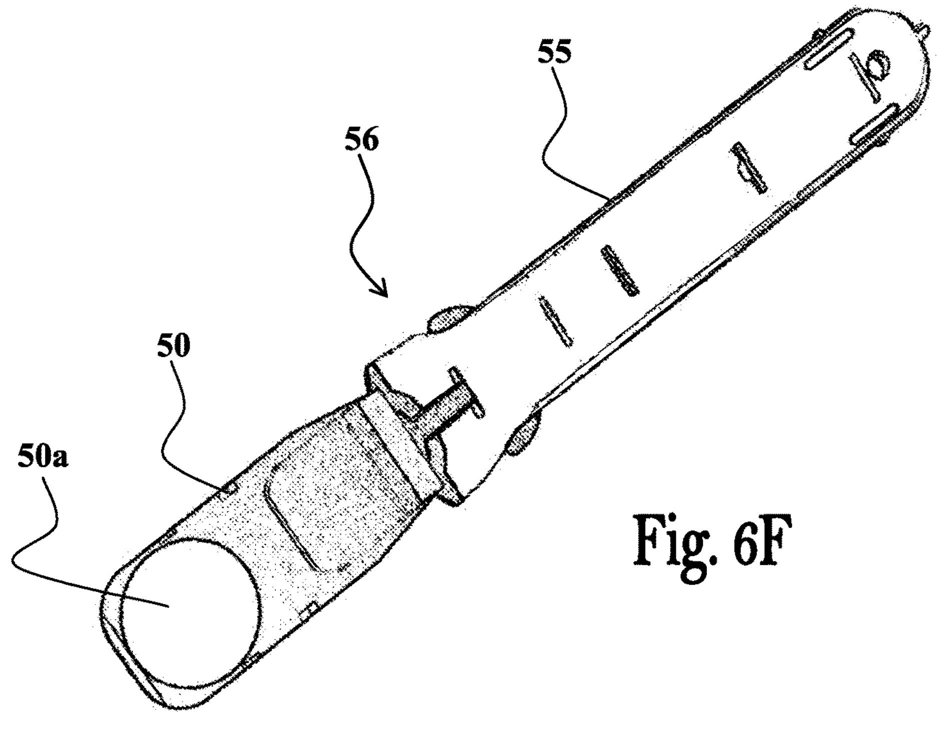

FIGS. 6E and 6F demonstrate another embodiment of the two part sample collection accessory 50 implemented with a quick connector unit 56 (e.g., snap buckle). For example, and without being limiting, in FIGS. 6E-F, the sample collection accessory 50 is connectable to the extension 55 by a quick connector 56 having a mail connector part 56*m* provided at a proximal end of the sample collection accessory 50, and a female connector part 56*f* provided at a distal end of the extension 55. FIG. 6F shows the sample collection accessory 50 connected to the extension 55 by the quick connector 56. FIG. 6E further illustrates an implementation of the plug 51 having an elongated grip element 51*j* configured to be received in one or more slots 51*s* formed along the extension 55. The slots 51*s* are configured to receive and slidably attach the plug 51 to the extension 55, and permit sliding it distally towards the hole 50*a* for placing it thereinside during the sample collection process, and thereafter slidably retracting it proximally, while maintaining its attachment to the extension unit 55.

Figure 7A:
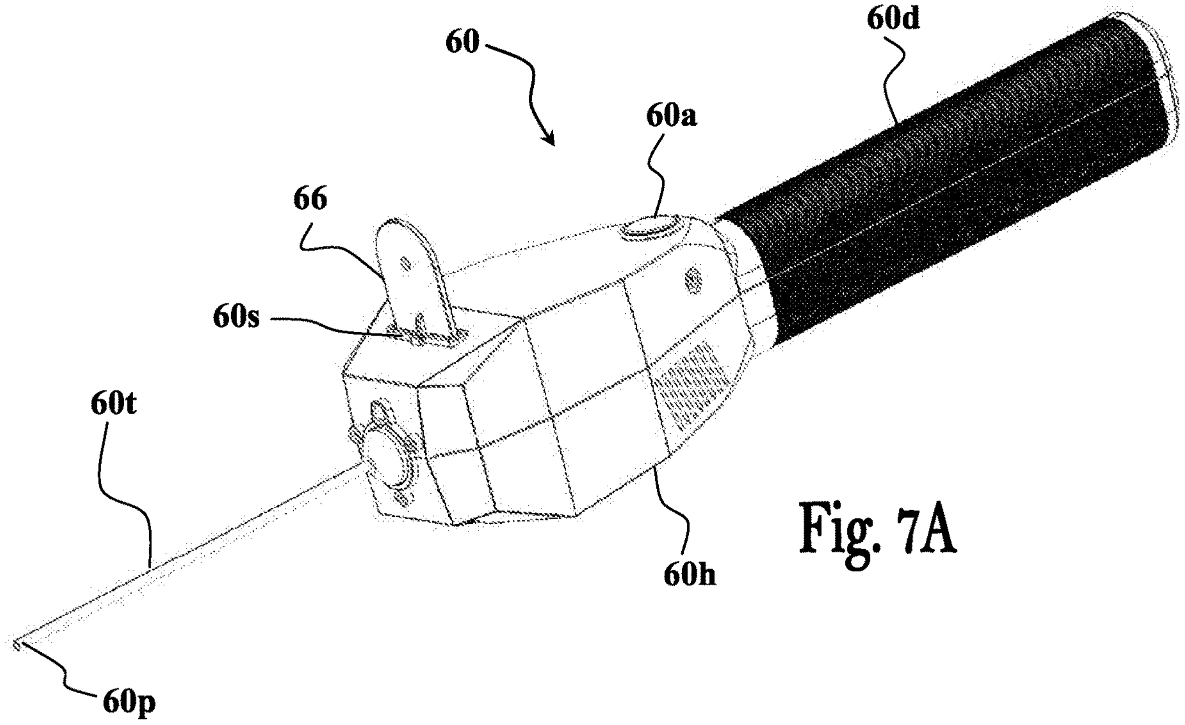
FIGS. 7A and 7B show perspective views of a sample collection unit usable for collecting samples from inside of hollow/sealed objects.
Figure 7B:
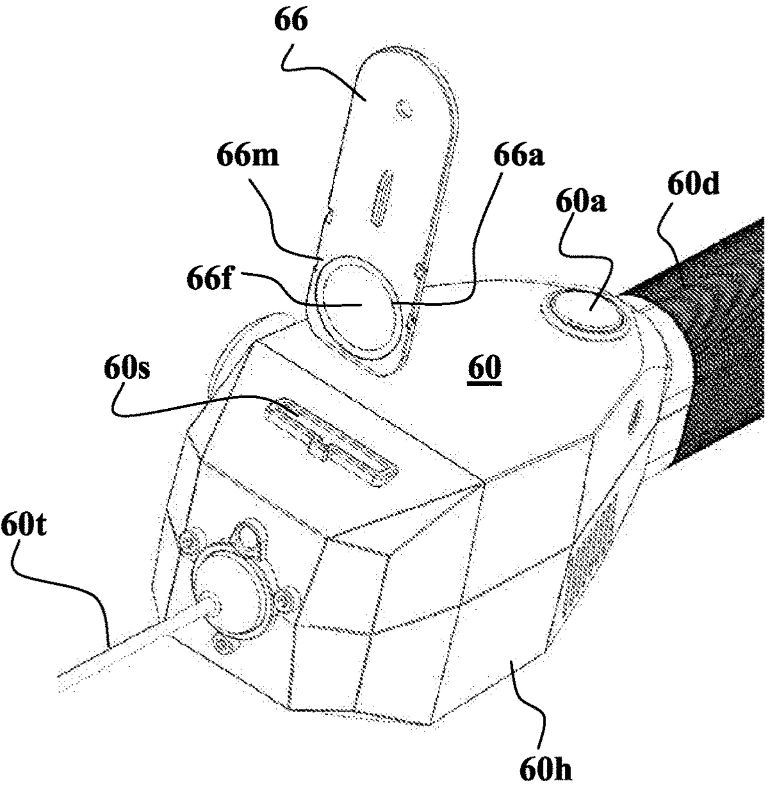

FIGS. 7A and 7B illustrate a handheld sample collection unit 60, particularly usable for collection of sample material from interiors of closed, or difficult to access, items (e.g., packages, containers, envelops, and suchlike). Sample collecting unit 60 generally comprises a handle 60*d* connected at one end of a housing 60*h* in which a vacuum pump (not shown) is installed, and a hollow tube 60*t* connected at another end of the housing 60*h*. The housing 60*h* comprises an activation button 60*a* and a slot 60*s* for introducing a sample collecting portion 66*m* of a sample collecting member 66 thereinto for collecting sample material. A piece of flexible/elastic absorbent/porous material 66*f* attached in a hole 66*a* formed in the sample collecting portion 66*m* is used to collect sample material by placing it inside the housing 60*h* in contact with a stream of air sucked thereinto by the sample collecting unit 60 through the tube 60*t*.

Sample collection using the sample collecting unit 60 may be thus carried out by introducing a sample collecting portion 66*m* of a sample collecting member 66 through the slot 60*s*, introducing the hollow tube 60*t* inside a cavity/hollow of an inspected item, and using the activation button to activate the vacuum pump to inject a stream of air into the housing 60*h* through the tube 60*t*. The stream of air received inside the unit 60 is passed through, or along, the sample collecting material 66*f* such that sample material carried by the streamed air is attached thereto. The operation of the vacuum pump may be then stopped and the sample collecting member 66 is removed from the slot 60*s* and introduced via the opening 12*p* of the sample inlet 12 of the substance detection device 10 into the sample inspection assembly 20 for carrying out vapor production and inspection, as described hereinabove.

In some embodiments the hollow tube 60*t* is configured in the form of a narrow puncturing needle, to thereby enable suction of sample material into the sample collection unit 60 from closed items (e.g., envelopes, packages). For example, and without being limiting, the tip 60*p* of the tube 60*t* may comprise a piercing edge (not shown) capable of piercing and introducing tube 60*t* through the enclosing material (e.g., package or envelope walls) of the inspected item. The suction pump of the sample collection unit 60 may be then activated to withdraw sample material from the interior of the inspected item and collect it onto the sample collecting material 66*f*.

It is noted that the hollow tube 60*t* may be configured for rapid replacement with various different types of tubes having specific configurations (e.g., lengths and/or inner diameters) for sampling air/gases from various different types of objects, such as but not limited to, cars, trucks, cargo, and the like.

Figure 8A:
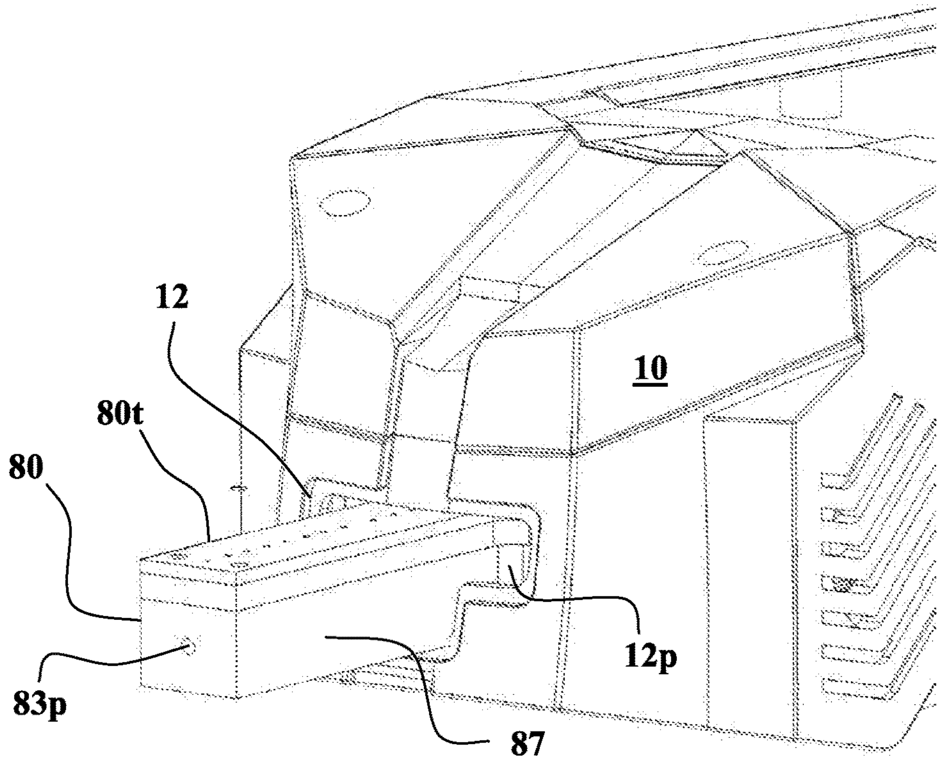
Figure 8B:
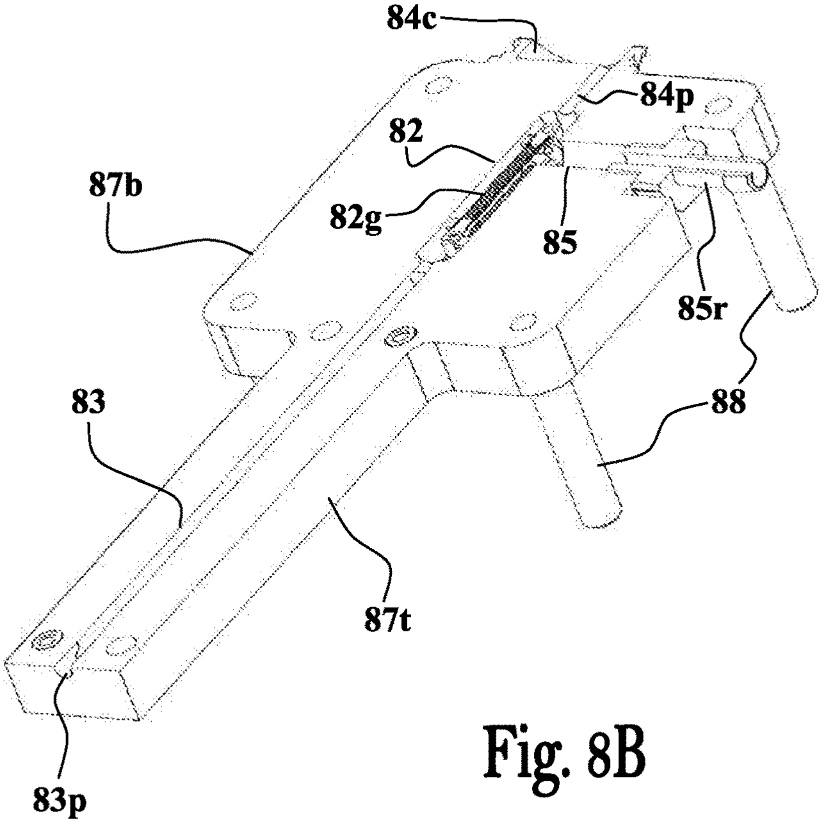

FIGS. 8A to 8C schematically illustrate a substance inspection accessory 80 having internal sensing and vapor production elements. As exemplified in FIG. 8A, the substance inspection accessory 80 may be attached to the substance detection device 10 such that a neck portion 87*t* thereof protrudes via the opening 12*p* of the device 10. With reference to FIGS. 8A and 8B, the substance inspection accessory 80 comprises a housing 87 having a main body portion 87*b* and the neck portion 87*t* extending therefrom. The distal end of the neck portion 87*t* includes an opening

83*p* through which air/gas sample is drawn into the substance inspection accessory 80. An elongated channel 83 formed in the neck portion 80*t* of the substance inspection accessory 80 connects the distal opening 83*p* with an elongated cavity 82 formed in the main body portion 87*b* and in which one or more heating elements 82*g* are installed. A proximal passage 84*p* formed in a proximal portion of the main body 87*b* communicates between the elongated cavity 82 and a pressure port 84*c*. In some embodiments the pressure port 84*c* is configured and operable for direct connection to the air pump 27, which may be operated to apply negative or positive pressure conditions inside the elongated cavity 82.

A lateral passage 85 formed in the main body portion 87*b* communicates the elongated boot 82 with an air/gas port 85*r* used for carrying out decontamination (regeneration) procedures for expelling sample/vapor material from the sample inspection accessory 80. As seen in FIG. 8C, a plurality of substance sensing elements 89 may be mounted spaced apart along the elongated channel 83 (e.g., lined up in a row) such that air/gas drawn into the sample inspection accessory 80 interacts with the substance sensing elements 89 during its passage through the channel 83. Terminals 89*t* of the substance sensing elements 89 protruding upwardly through the channel 83 are received and electrically connected to circuitry provided in a PCB 87*c* at the upper portion of the accessory 80. The PCB 87*c* is configured to connect to the control unit 45 and/or the batteries 32 (or any other power source) for powering the circuitry provided thereon.

During sample collection the heating devices 82*g* may be activated to heat the neck portion 87*t* of the accessory 80, and the air pump 27 of the substance detection device 10 is activated to draw a stream of air/gas (e.g., by proximally pulling the piston 27*p*) into the accessory 80. The heating elements 82*g* are configured and operable to heat the entire accessory 80 structure (i.e., the body 87*b* and neck 87*t* portions). Thus, the air/gas drawn through the opening 83*p* into the sample inspection accessory 80 is heated during passage through the neck portion 87*t* to produce vapors therefrom, said air/gas and vapors interacting with the sensing elements 89 situated in the channel 83.

In some possible embodiments one or more temperature sensors (not shown e.g., thermocouples) may be used in the accessory 80 to allow automatic temperature stabilization thereof by the control unit 45. For example, and without being limiting, a temperature sensor may be mounted inside the elongated channel 83, in the elongated cavity 82, and/or in the PCB 87*c*. The control unit may be thus configured and operable to receive through electrical connector 42 of the accessory 80 the temperature measurements generated by the temperature sensors and controllably operate the heating elements 82*g* to maintain a substantially constant predetermined temperature level inside the accessory 80.

After measuring the reaction of the sensing elements 89 to the drawn sample a cleaning/decontamination process is performed using air pump 27 connected to the pressure port 84*c*. Additionally or alternatively, the cleaning/decontamination process may be performed using the pump 49 connected to the air/gas port 85*r*. For example, and without being limiting, the decontamination process may comprise activating the air pump 27 to expel any sample/vapor material through the opening 83*p* by streaming gas/air (e.g., by proximally pushing the piston 27*p*) via the proximal passage 84*p*, elongated cavity 82 and elongated channel 83. Similarly, the pump 49 may be activated, before, after, or simultaneously with, pump 27, to expel any sample/vapors from the sample inspection accessory 80 via its opening 83*p*.

The heating elements 82*g* may be also activated during part, or the entire duration of the decontamination process to heat the sensing elements 89 and disengage and expel any substance particles that became bound to them during the sample detection stage.

The linear arrangement of sensors 89 was used in an experiment to analyze the sorption properties of adsorbents deposited on the surface of the sensitive sensors, depending on the speed of flow (supply) of the analyzed substance, and on the concentration and location of sensors with respect to the inlet through which the analyzed substance (or sample) is inserted.

The linear arrangement of the sensing elements 89 may be used to analyze the sorption properties of adsorbents deposited on the surface of the sensing elements, depending on the speed of flow (supply) of the sample along the channel 83, and the concentration and location of sensing elements with respect to the inlet through which the sample is inserted. The linear array of the sensing elements may be used for detection of different foreign substances in a sample. In this case the sensing elements in the linear array are configured to adsorb different substances (e.g., electrodes of the sensing elements are formed with different coatings). Hence, when the sample flows through the channel 83 the different substances contained in the sample are sequentially adsorbed by the respective sensing element(s) in the array.

The sample collection accessory 80 thus permits adding substance sensing elements 89 to the sensing elements provided in the sensor arrangement 22 of the device 10. In some embodiments the sample collection accessory 80 is connected inside the sample detection device 10 and replaces the sample inspection assembly 20 i.e., substance detection is performed using the sensing elements 89 only.

In this non limiting example the accessory 80 comprises eight sensing elements 89, but it may be configured to include any other suitable number of sensing elements 89 (e.g., 1-7, 9-16, or more). The control unit 45 may be configured to select measurement data generated by one or more, or all, of sensing elements 89 in the data processing and analysis stages when determining the presence of specific substances in the sample. In some embodiments the control unit 45 may combine measurement data generated by one or more of the sensing elements 89 with measurement data generated from the same sample by the sensing elements (22*y*) of the sensor array 22.

It is noted that the linear arrangement of the sensing elements 89 exemplified in FIG. 8C guarantees that the sample drawn into the accessory 80 is in contact with and interacts with all the sensing elements 89, and thus provides for maximal exploitation of the sample and improved sensitivity. This configuration also permits sample collection and interaction (with the sensing elements) at room temperature of a desirable working environment.

FIG. 9 is a flow chart illustrating a substance detection cycle 70 using the sample detection device 10, according to some possible embodiments. The detection cycle 70 may be initiated in step 71*a* by collecting sample material into the sample inspection assembly 20 directly through the sample inlet 12, or in step 71*b* by collecting sample material and/or its vapors using a sample collection accessory/unit, as described hereinabove with reference to FIGS. 5-7. In step 72 vapors are produced from the sample material by the vapor production unit 23*c*. It is noted that step 72 is optional, and in certain detection cycles it may be skipped (e.g., if inspecting heated surface/liquids, or when using the sample collecting accessory 40 shown in FIG. 5).

In step 73 the vapors are drawn into the gas chamber 23*r* and flow into the sensor arrangement 22. Next, in step 74, the reaction of the substance sensing elements to the vapors is measured and data indicative thereof is generated, and in step 75 the generated data is processed and analyzed to determine the presence or absence of one or more specific substances therein.

A discharge and cleaning/decontamination sequence is initiated in steps 76-77 in which the vapor/sample is discharged from the gas chamber and the substance sensing elements are heated to disengage particles bound to them during the substance detection step. Thereafter, in step 78 positive pressure conditions are applied inside the gas chamber 23*r* until a predetermined pressure level is reached for causing, in step 79, instant discharge of the built-up pressure via the outlet port 23*g* of the gas chamber 23*r*. After step 79 the sensor array 22 and the sensing elements 22*y* are cleaned from sample/vapor and the heating and pressure building operations in the gas chamber 23*r* can be stopped. In this state the device 10 is ready to carry out a new detection cycle by passing the control back to step 71*a* or 71*b*.

Figure 10A:
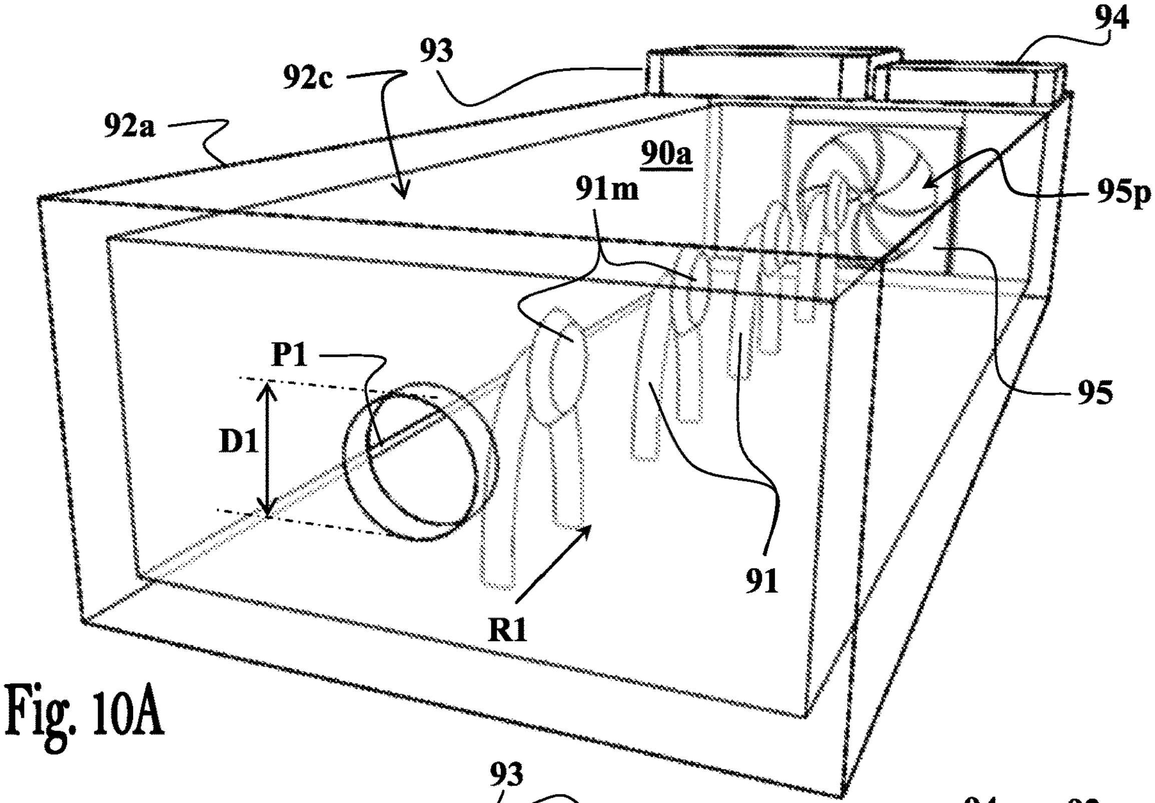
FIGS. 10A to 10C schematically illustrate a miniature substance detection device according to possible embodiments, wherein FIG. 10A exemplifies a miniature substance detection device having a single row of sensors (linear array), FIG. 10B exemplifies a miniature substance detection device having a two dimensional array of several rows of sensors.
Figure 10B:
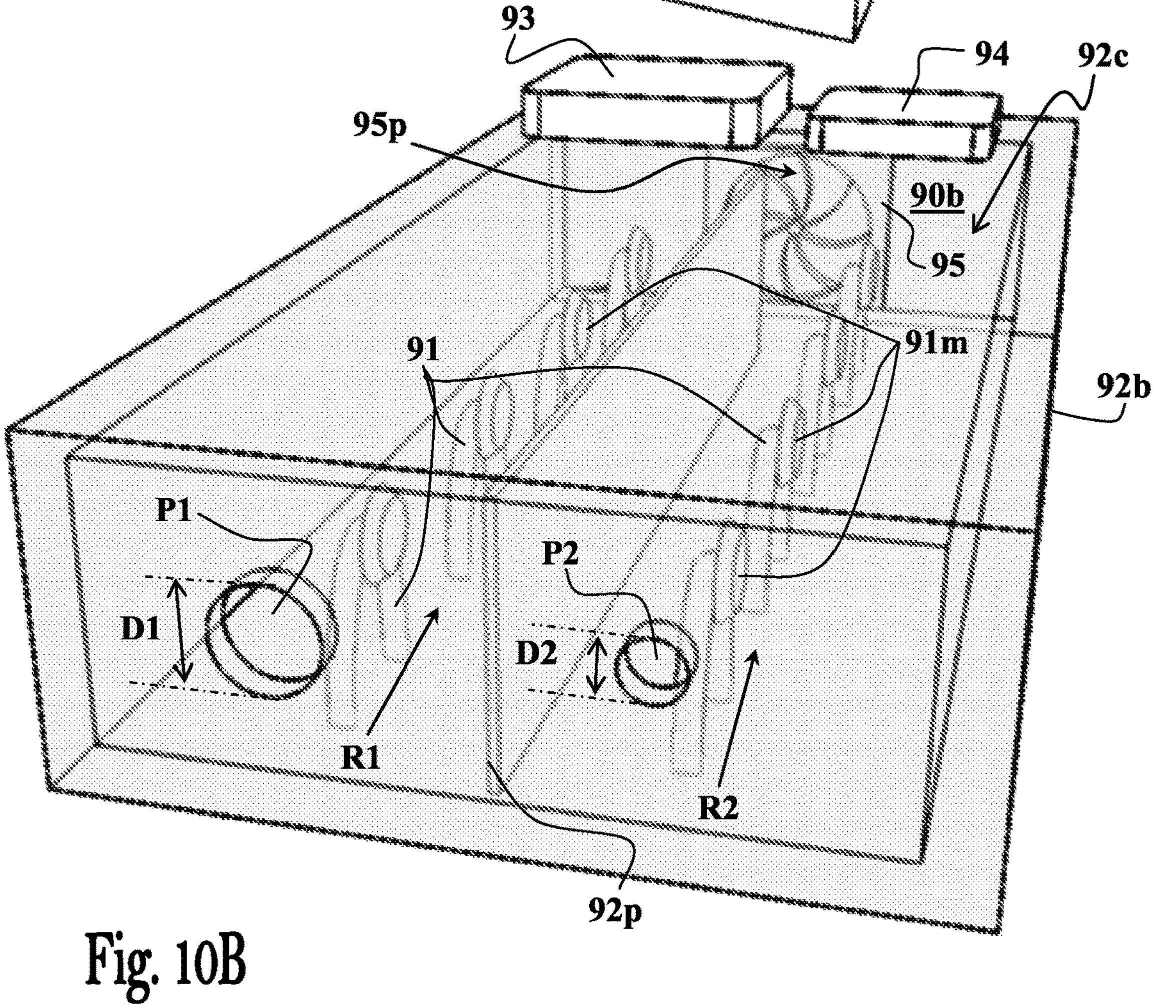

FIGS. 10A and 10B show perspective views of miniature substance detection devices according to some possible embodiments, configured and operable to detect/identify one or more certain materials in a stream of fluid (e.g., gaseous phase at room temperature, such as ambient air) drawn thereinto. The miniature substance detection device 90*a* shown in FIG. 10A comprises a row (linear array) R1 of substance sensing elements 91 operably mounted inside a housing 92*a* for interaction with gaseous sample material introduced thereinto. In this non-limiting example the housing 92*a* is an elongated hollow structure configured to define an elongated chamber 92*c* having openings at its extremities comprising a front inlet opening P1 (also referred to herein as a sample inlet) and a rear outlet opening 95*p*. Inlet opening P1 is provided at a predetermined location in a wall at one end (front side) of the housing 92*a* so as to be aligned with the location of sensory portions 91*m* (e.g., having piezoelectric resonator crystals) of the sensing elements 91. Outlet opening 95*p* is provided in a wall at the other end (rear side) of the housing 92*a*, in which a pressure device 95 (e.g., pump, blower or fan) is sealably mounted for drawing a stream of fluid (air) into the housing 92*a* through the inlet opening P1.

The miniature substance detection device 90*a* further comprises a control unit 93, a wireless communication module 94 (e.g., Bluetooth, ZigBee, WiFi, NFC, RFID, cellular communication) electrically coupled to control unit 93, and a power source (not shown e.g., one or more batteries) for providing power to the device's components. The control unit 93 is configured and operable to actuate the pressure device 95 and the sensing elements 91, and receive measurement data from the sensing elements 91 indicative of the presence of one or more certain materials in the stream of fluid drawn into the elongated chamber 92*c*. The control unit 93 may be configured to process the measurement data received from the sensing elements 91 and/or transmit (e.g., wirelessly) the measurement/processed data to a remote or local computer system (96 in FIG. 10C) for further processing and/or presentation to a user. Optionally, and in some embodiments preferably, each one of the sensing elements 91 is configured for detection/identification of a specific material, or group of materials having one or more common chemical and/or physical properties.

FIG. 10B exemplifies another possible embodiment of a miniature substance detection device 90*b* comprising a two-dimensional array of sensing elements 91 operably mounted inside an elongated housing 92*b* for identification/detection of one or more certain materials in a stream of fluid drawn thereinto. In this specific and non-limiting example the array of sensing elements 91 includes only two rows, R1 and R2, of sensing elements 91. It should be however clear that the sensor array may similarly include more than two rows of sensing elements, and correspondingly a respective number of inlet openings. The rows, R1, R2, . . . , of sensing elements 91 are arranged inside the elongated chamber 92*c* one parallel to the other in front of respective inlet openings, P1, P2, . . . . The height of the inlet openings, P1, P2, . . . , (e.g., the centers of the inlet opening) corresponds to the height of the sensory portions 91*m* of the sensing elements 91. The miniature substance detection device 90*b* also comprises a control unit 93, a wireless communication module 94 electrically coupled to the control unit 93, and a power source (not shown). The inlet openings P1, P2, . . . , are positioned at the front side of the housing and a pressure device 95 is sealably mounted in an outlet opening 95*p* at the rear side of the housing 92*b*.

As exemplified in FIG. 10B, the inlet openings, P1, P2, . . . , of the respective sensing elements rows, R1, R2, . . . , may be of different diameters, D1, D2, . . . . In this way, the device 90*b* is adapted to introduce a respective number (in this example two) of different fluid streams having different flow rates into the chamber 92*c* upon activation of the pressure device 95, thereby providing improved control over the air inflow/sample inflow onto each sensor row, R1, R2, . . . , residing inside the chamber 92*c* and over the exposure time of the sensors elements to the sample inflow. For this purpose one or more partitions 92*p* may be installed inside the chamber between the sensor row, R1, R2, . . . , to thereby define a number sample flow paths therebetween corresponding to the number of sensor row, R1, R2, . . . , and optionally to further prevent turbulences thereinside.

In some embodiments the row (R1, R2, . . . ) of the sensor array is configured as a modular structure to form replaceable sensing elements rows allowing for easy and quick replacement of any one of the rows of sensing elements of the array of sensing elements 91. In this way the substance detection and identification device 90*b* may be quickly adapted for detection of different types of materials by replacing one or more replaceable rows of sensing elements of the array with other replaceable sensing elements rows carrying particular types of sensing elements for detection and identification of particular substances. Accordingly, the substance detection and identification device 90*b* may be quickly adapted for various different purposes/applications, such as, but not limited to, wine testing, explosive detection, narcotic detection, and suchlike, by simply replacing one or more of the rows R1, R2, . . . of sensing elements of the array.

The miniature substance detection device 90*a* or 90*b* (collectively referenced 90) may be implemented to provide a relatively small and portable unit, for example and without being limiting, as a keychain gadget. As seen in FIGS. 10A and 10B the sensory portions 91*m* of the sensor elements, and the body (e.g., inverted "U"-like shaped element) of the sensor elements 91 are located in parallel (or conjugating) planes such that they are substantially parallel to the sample flow paths (R1, R2, . . . ), and in this way the surface areas of the sensing elements 91, and of the sensory portions 91*m*, facing the sample stream are minimized and correspondingly obstructions to the sample flow inside the chamber 92*c* are substantially minimized. In another non-limiting example, the sensor rows, R1, R2, . . . , may be arranged inside the chamber 92*c* similar to the arrangement of substance sensing elements 89 exemplified in FIG. 8C.

It is however noted that the geometrical shape of the sample inlet openings P1, P2, . . . , is not necessarily circular, and that other possible shapes may be equally used for the sample inlet openings P1, P2, . . . , such as, but not limited to, rectangular, triangular elliptic, pentagon, and any combination thereof. For example, and without being limiting, in some embodiments sample inlet openings P1, P2, . . . , are shaped in the form of vertical rectangular slots having a length of about 5 mm and a width of about 0.3 mm. Proper adjustment of the geometrical shapes of the sample inlet openings P1, P2, . . . , further improves control over the flow rates of the fluid streams drawn into the chamber 92*c* and along the sample flow paths, and the absorption time of the drawn sample by the sensing elements 91.

In some embodiments the substance detection devices 90 may be further configured to perform a regeneration cycle after carrying out a sample detection cycle to discharge/expel the sample and decontaminate the chamber 92*c*. For example, and without being limiting, the control init 93 may be configured to actuate the pressure device 95 to perform a suction operation during the sample detection cycles in order to draw one or more fluid streams into the chamber 92*c*, and thereafter actuate the pressure device 95 to perform a discharge operation (e.g., using a blower/fan and changing the direction of fan rotations according to desired operation mode) during the regeneration cycles in order to expel one or more fluid streams out of the chamber 92*c*. In some possible embodiments the substance detection devices 90 further comprises a heating unit (not shown) mounted behind the pressure device 95 (i.e., external to the chamber) 92*c*, for heating a stream of fluid streamed into the chamber 92*c* through the rear outlet opening 95*p* during the regeneration cycles and thereby remove and disengage sample material that become attached to the sensing elements 91.

In some embodiments the control unit 93 is further configured to controllably adjust the rotation speed of a fan device of the pressure unit 95 and to thereby control the flow rate of the one or more fluid streams drawn into the chamber 92*c* and which flows along the sample flow paths, and thereby improve control over the absorption speed of the sample material by the sensing elements 91.

Figure 10C:
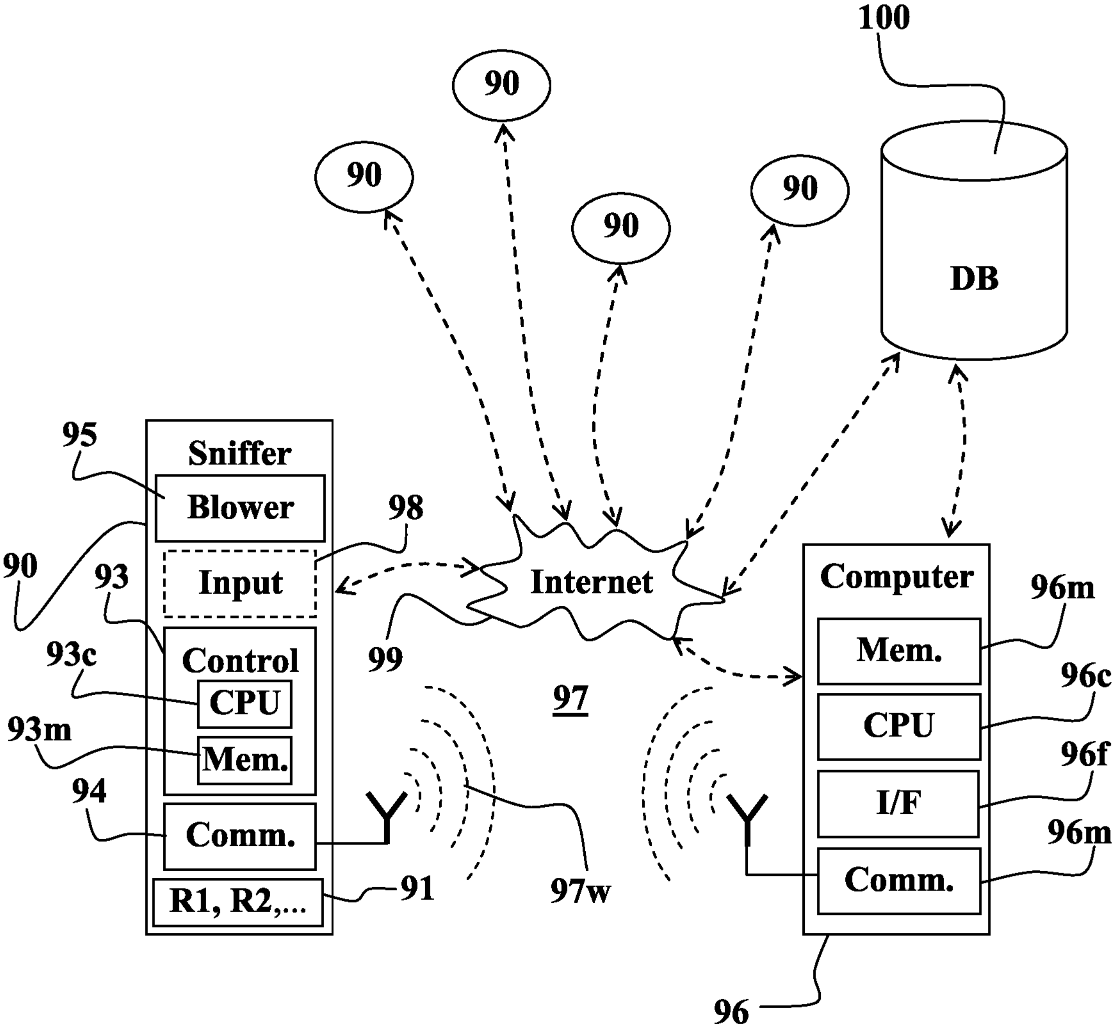

FIG. 10C is a block diagram exemplifying a monitoring system 97 utilizing one or more miniature substance detection devices 90 as exemplified in FIGS. 10A and 10B. In this non-limiting example, the communication module 94 of the substance detection devices 90 is adapted to communicate with a computer system 96 (e.g., desktop, laptop, or server computer, or any type of smart device such as a smart-phone or tablet) by direct wireless communication 97*w*, and/or over a computer network (e.g., the Internet) 99. The control unit 93 of the miniature substance detection device 90 comprises a processing utility 93*c* and a memory utility 93*m* configured and operable to receive an actuation signal (e.g., via the communication module 94), and responsively activate the pressure device 95 and the sensing elements 91, receive measurement data from sensing elements 91, process the received measurement data and/or transfer the same to the computer 96 through the communication module 94 for processing.

As exemplified in FIG. 10C, the miniature substance detection device 90 may further comprise an input module 98 (e.g., activation switch) electrically coupled to the control unit 93 and configured and operable to generate an activation signal initiated by a user of the device.

The computer system 96 comprises a processing utility 96*c* and a memory utility 96*m* configured and operable to receive and process the measurement data via a communication module 96*m* thereof, and output the processed and/or received measurement data, and/or corresponding alerts, via a user interface unit 96*f* (e.g., using any suitable visual and/or audible output device, such as video/LCD display and/or speakers). The user interface unit 96*f* may be further adapted to receive a user's input (e.g., using a keyboard/keypad, touchscreen, and/or a pointing device) usable for generation of an activation signal to be transferred to the miniature substance detection device 90 through the communication modules 96*m* and 94.

The monitoring system 97 may be configured for detection and identification of different types of materials, and in some embodiments it may be specialized for use in specific substance detection and identification application, such as, but not limited to, food safety and beverages inspection (e.g., water, wines, alcohol, dairy products, fruits and vegetables, and suchlike), and/or security screening (e.g., explosives detection, narcotics and contraband detection), and/or bio-medical diagnostics (e.g., breath, urine, lung cancer, tuberculosis and suchlike). In such applications the computer system 96 may be implemented by a smart device (e.g., smart phone, tablet, PDA, and suchlike), a laptop or desktop computer, for example.

Alternatively, the monitoring system 97 may be configured to implement an environmental monitoring system for detection and identification of the presence and/or concentration of specific material types (e.g., pollutants, smoke, allergens, etc.) e.g., by using a plurality of substance detection devices 90 distributed over predefined geographical regions. The monitoring system 97 may thus comprise a data storage system 100 (e.g., database server), accessible by the computer system 97 e.g., directly over communication wires/bus or wirelessly, and/or over the computer network 99. Alternatively, the data storage system 100 may be part of the computer system 97. The data storage system 100 may be used to store measurement data collected from the plurality of substance detection devices 90 over time, and other data, which may be used by the computer system for generating reports and statistical analysis.

Functions of the system described hereinabove may be controlled through instructions executed by a computer-based control unit (45 or 93). A control unit suitable for use with embodiments described hereinabove may include, for example, one or more processors connected to a communication bus, one or more volatile memories (e.g., random access memory—RAM) or non-volatile memories (e.g., Flash memory).

A secondary memory (e.g., a hard disk drive, a removable storage drive, and/or removable memory chip such as an EPROM, PROM or Flash memory) may be used for storing data, computer programs or other instructions, to be loaded into the computer system.

For example, computer programs (e.g., computer control logic) may be loaded from the secondary memory into a main memory (e.g., 93*m*) for execution by one or more processors of the control unit. Alternatively or additionally, computer programs may be received via a communication interface (e.g., 94). Such computer programs, when executed, enable the computer system to perform certain features of the present invention as discussed herein. In particular, the computer programs, when executed, enable a processing unit to perform and/or cause the performance of features of the present invention. Accordingly, such computer programs may implement controllers of the computer system.

In an embodiment where the invention is implemented using software, the software can be stored in a computer program product and loaded into the computer system using the removable storage drive, the memory chips or the communications interface. The control logic (software), when executed by the processor, causes the control unit to perform certain functions of the invention as described hereinabove.

In another embodiment, features of the invention are implemented primarily in hardware, using, for example, hardware components such as application specific integrated circuits (ASICs) or field-programmable gated arrays (FPGAs).

Implementation of a hardware state machine for carrying out the functions described herein will be apparent to persons skilled in the relevant art(s). In yet another embodiment, features of the invention can be implemented using a combination of both hardware and software.

Figure 11:
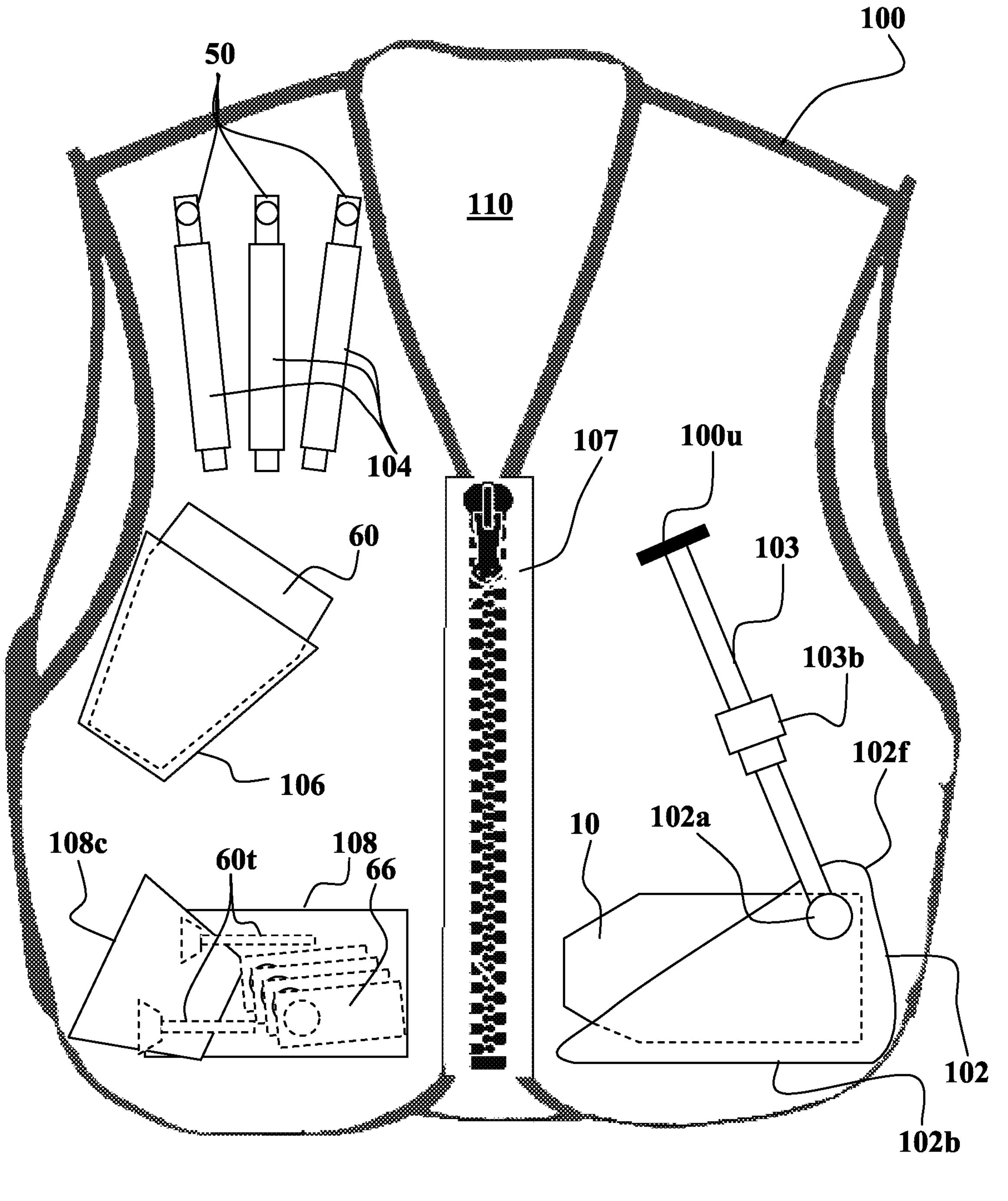
FIG. 11 schematically illustrates a wearable article usable for carrying and quick utilization of the substance detection device, the sample collecting unit, and various accessories thereof, as depicted in FIGS. 1A 5-6 and 7-8.

FIG. 11 schematically illustrates a kit 110 for use in detection of foreign substances according to some possible embodiments. In this non-limiting example a wearable article 100 (e.g., vest) is used for carrying the substance detection device 10 and its accessories, the sample collection unit 60, and other parts of these units as well. The wearable article 100 comprises at one side a flap 102 attached to a lower portion 102*b* of the wearable article 100 (e.g., over a lower abdomen region of the user) configured to form a pocket for holding the substance detection device 10. A free end 102*f* of the flap 102 is detachably attached to an upper portion 100*u* of the wearable article 100 by a strap 103 having a connector (e.g., bolt) at a free end thereof configured to connect to the substance detection device 10 (e.g., by screwing) and thereby form the pocket in which the substance detection device 10 is held and secured thereinside. The strap 103 may comprise an adjustable connector 103*b* (e.g., adjustable buckle) configured to enable quick opening of the pocket formed by the flap 102 and adjusting the length of the strap 103.

The other side of the wearable article 100 comprises a pocket 106 formed over a central portion of the wearable article 100 (e.g., located over ribs of the user) and configured to receive and hold the handheld sample collection unit 60 thereinside. As shown, one or more holders 104 for sample collection accessories 50 are provided above the pocket 106 (e.g., over a chest region of the user), and a pouch 108 is provided below the pocket 106 (e.g., at a lower abdomen region of the user) for various parts/elements of the substance detection device 10 and/or the sample collection unit 60. In this non-limiting example the pouch 108 holds one or more sample collecting members 66 for the substance detection device 10 and one or more hollow tubes 60*t*, having different lengths, for the sample collection unit 60. Additionally or alternatively, one or more sample collecting accessories 50 and or substance inspection accessories 80 may be placed inside the pouch 108. The wearable article 100 may comprise a fastener 107 (e.g., zipper, Velcro, or suchlike) for securing it over the body of the user (not shown).

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A substance detection and identification device, comprising:

a housing having a sample inlet configured for passage of a sample material therethrough;

a sensing unit located in a chamber in said housing and comprising a vessel containing a circular array of sensing elements arranged around an axis, each of said sensing elements configured and operable to interact with the sample material in a vicinity thereof for detecting one or more specific substances and generating sensing data indicative thereof, said vessel being formed with an array of apertures arranged around the axis, each of said apertures being aligned with one of said sensing elements, said apertures serving as gas inlets for passage of the sample material towards the respective sensing elements resulting in substantially concurrent supply of the sample material to the sensing elements, and serving as gas outlets for facilitating flow of the sample material from the sensing elements, said chamber comprising a one way outlet valve configured and operable to permit discharge of the sample material from said chamber;

a sample path passing within said housing between the sample inlet and the circular array of sensing elements, for facilitating flow of the sample material towards the sensing unit;

a heating unit configured and operable to heat at least one of said sensing elements and/or the sample material; and a pressure unit configured to attract the flow of the sample material along said sample path into said sensing unit, and cause flow of the sample material from the sensing elements to discharge from said housing.

2. The device according to claim 1, wherein said chamber is configured for removably mounting the sensing unit therein.

3. The device according to claim 1, wherein the heating unit and the housing are configured for removably mounting the heating unit in the housing in the vicinity of the sensing unit.

4. The device according to claim 1, wherein the heating unit is configured with a geometry matching that of an arrangement of the sensing elements in said sensing unit.

5. The device according to claim 1, wherein the one way outlet valve is configured and operable to respond to a predetermined pressure level inside the chamber for selectively shifting from its normally closed state to an open state to permit discharge of the sample material from said chamber.

6. The device according to claim 1, wherein said heating unit is configured and operable to receive the sample material drawn through said sample inlet in the housing and produce a vapor thereof.

7. The device according to claim 6, wherein the heating unit comprises a first heater configured and operable for heating said sensing elements to physically separate between the sample material and the sensing elements, and a second heater for producing the vapor of the received sample material.

8. The device according to claim 6, wherein the heating unit comprises a heater configured and operable for selectively producing the vapor of the received sample material for interaction with the sensing elements, and for heating said sensing elements to physically separate between the sample material and the sensing elements.

9. The device according to claim 1, wherein each of the sensing elements is accommodated in a dedicated compartment of the sensing unit defining the vicinity of the sensing element, the compartment being formed with the array of apertures for passage of the sample material into and out of the compartment.

10. The device according to claim 1, wherein the sample inlet in the housing is configured to sealably connect to a sample collection accessory, and wherein said pressure unit is operable for drawing the sample material therefrom through said sample inlet.

11. The device according to claim 10, wherein said device is configured to receive a stream of ambient air with the sample material from the sample collection accessory connected to said sample inlet.

12. The device according to claim 11, comprising an electrical connector in, or near, the sample inlet, configured and operable to establish an electrical connection with the sample collection accessory when the sample collection accessory is connected to said sample inlet.

13. The device of claim 1, comprising a control unit configured and operable to activate the pressure unit for drawing the sample material through the sample path into the sensing unit for interaction with the sensing elements, and to receive and process the sensing data generated by the sensing elements and determine the presence of one or more specific substances in said sample material.

14. The device of claim 13, wherein the control unit is configured and operable to activate the heating unit for physically separating between the sample material and the sensing elements, and thereafter activate the pressure unit for applying a pressure to discharge the separated sample material from the sensing unit.

15. The device of claim 13, further comprising a communication module configured and operable to receive data associated with the sensing data from the control unit and transmit the same to a computer system.

16. The device of claim 15, wherein the communication module is configured and operable to transmit the data associated with the sensing data received from the control unit to one of the following: a smart device, a desktop computer, a laptop, or a remote server.

17. The device of claim 15, wherein the communication module is configured and operable for wireless data communication.

18. A monitoring system comprising:

a plurality of substance detection and identification devices according to claim 15;

a computer system configured and operable to receive and process the data associated with the sensing data transmitted from the plurality of substance detection and identification devices and generate corresponding indications to a user; and a data storage system for storing the data associated with the sensing data received from the plurality of substance detection and identification devices.

19. A kit for use in detection of foreign substances, the kit comprising:

the substance detection and identification device of claim 13, wherein the sample inlet is configured to sealably connect to a sample collection accessory selected from a set of sample collection accessories, thereby enabling to receive a flow of the sample material from the sample collection accessory by pressure; and said set of sample collection accessories each configured to collect the sample material from a vicinity thereof and, when connected to said housing, deliver the collected sample material through said sample inlet.

20. The kit according to claim 19, wherein said set of sample collection accessories comprises a sample collection accessory configured as a handheld unit having a handle at a proximate portion thereof and a sample collector at a distal portion thereof, said sample collector being configured for adsorbing a sample material thereon, and for said sealable connection to the sample inlet of the housing.

21. The kit according to claim 20, wherein said sample collection accessory of the set of sample collection accessories is further configured for removably attaching the handle to the proximate portion thereof, thereby enabling replacement of the handle.

22. The kit according to claim 21, comprising a set of handles of different sizes.

23. The kit according to claim 19, comprising a set of sample collection accessories for drawing ambient air with the sample material therethrough, the sample collection accessories of said set differing from one another in at least a length thereof.

24. The kit according to claim 19, comprising a belt fastening arrangement configured for carrying the substance detection and identification device and for fastening it to a belt worn by a user.

25. The kit according to claim 19 comprising a charger for charging a rechargeable power source of the substance detection and identification device.

26. The kit according to claim 19 comprising a handheld unit configured for collecting a sample material from a vicinity thereof by suction onto a sample collector portion of one of the sample collection accessories, thereby enabling absorbance of the sample material collected by the handheld unit onto said sample collector portion.

27. The kit according to claim 26, wherein said handheld unit has a handle at a proximate portion thereof, a tube at a distal end thereof, and contains a vacuum pump for suction of the sample material.

28. The kit according to claim 27, wherein said handheld unit is configured for removably attaching to the tube at the distal end thereof, thereof enabling replacement of the tube.

29. The kit according to claim 28, comprising a set of tubes of different sizes configured for removably attaching at the distal end of the handheld unit.

30. The kit according to claim 19, comprising a vest configured and operable for carrying at least some components of the kit.

31. A substance detection and identification device comprising:

a housing having a sample inlet configured for passage of a sample material therethrough;

a sensing unit comprising an array of sensing elements arranged in an array of a certain number of spaced-apart rows of sensing elements, each of said sensing elements configured and operable to interact with the sample material in a vicinity thereof for detecting one or more specific substances and generating sensing data indicative thereof;

a sample path connecting between the sample inlet and the sensing unit for facilitating passage of the sample material towards the sensing unit, said sample inlet being in the form of a certain number of inlet openings formed in a front side of said housing, each of the inlet openings being associated with one row of the sensing elements of said array of sensing elements; and a pump device configured and operable to draw a certain number of fluid streams into said housing, each fluid stream being drawn through a respective one of said inlet openings for interaction with the sensing elements of a respective row in said array, wherein at least some of the inlet openings have different sizes thereby affecting different flow rates of at least some of the fluid streams.

32. The device of claim 31, wherein each inlet opening in the front side of the housing is configured to direct a respective one of the fluid stream drawn from the inlet opening towards sensory portions of the sensing elements in the respective row associated with the inlet opening.

33. The device of claim 31, comprising a control unit configured and operable to actuate the pump device and the sensing elements, and receive and process the sensing data generated by the sensing elements responsive to the fluid streams drawn into the housing.

34. A kit for use in detection of foreign substances, the kit comprising:

the substance detection and identification device of claim 31 configured to sealably connect to a sample collection accessory selected from a set of sample collection accessories, said substance detection and identification device comprising a heating unit and a control unit configured and operable to activate the pump device to cause suction of the sample material through the sample inlet to thereby receive a sample flow from a sample collection accessory connected to the device and direct said sample flow to the sensing unit for interaction with the sensing elements, receive and process the sensing data generated by the sensing elements and determine the presence of one or more specific substances in said sample material, activate said heating unit for heating the drawn sample material or for physically separating between the sample material and said sensing elements, and activate said pump device to discharge the separated sample material by pressure from the sensing unit; and said set of sample collection accessories each configured to collect sample material from a vicinity thereof when connected to said housing.

35. The kit according to claim 34, wherein the housing comprises an electrical connector in, or near, the sample inlet, and said substance detection and identification device is configured and operable to establish electrical connection with one of the sample collection accessories via said electrical connector when the sample collection accessory is connected to said sample inlet.

36. The kit according to claim 35, wherein said control unit is configured and operable to identify the electrical connection with the sample collection accessory and operate an internal heating element thereof to produce vapors of the collected sample material.

37. The device of claim 31, comprising a control unit configured and operable to receive the sensing data generated by the sensing elements responsive to the fluid streams drawn into the housing, and communicate data associated with said sensing data to a monitoring system, said monitoring system configured to receive the data associated with the sensing data from a plurality of said substance detection and identification devices, and generate corresponding indications and/or store said data associated with the sensing data in a data storage system.

* * * * *